US006907279B2

(12) United States Patent
Sato et al.

(10) Patent No.: US 6,907,279 B2
(45) Date of Patent: Jun. 14, 2005

(54) OPTICAL SYSTEM FOR MEASURING METABOLISM IN A BODY

(75) Inventors: Hiroki Sato, Ohi (JP); Atsushi Maki, Fuchu (JP); Masashi Kiguchi, Kawagoe (JP)

(73) Assignees: Hitachi, Ltd., Tokyo (JP); Hitachi Medical Corporation, Tokyo (JP)

( * ) Notice: Subject to any disclaimer, the term of this patent is extended or adjusted under 35 U.S.C. 154(b) by 0 days.

(21) Appl. No.: 10/452,052

(22) Filed: Jun. 3, 2003

(65) Prior Publication Data

US 2004/0006260 A1 Jan. 8, 2004

(30) Foreign Application Priority Data

Jul. 8, 2002 (JP) .................................... 2002-198282

(51) Int. Cl.[7] .................................................. A61B 5/00
(52) U.S. Cl. ...................................... 600/322; 600/310
(58) Field of Search ................................ 600/309–310, 600/344, 322, 323

(56) References Cited

U.S. PATENT DOCUMENTS

| | | | | |
|---|---|---|---|---|
| 5,058,588 A | * | 10/1991 | Kaestle .......................... | 600/323 |
| 5,249,576 A | * | 10/1993 | Goldberger et al. ............ | 600/323 |
| 5,348,003 A | * | 9/1994 | Caro ............................. | 600/310 |
| 5,421,329 A | * | 6/1995 | Casciani et al. ............... | 600/131 |
| 5,776,060 A | * | 7/1998 | Smith et al. ................... | 600/340 |
| 5,803,908 A | * | 9/1998 | Steuer et al. .................. | 600/314 |
| 5,995,857 A | * | 11/1999 | Toomim et al. ................ | 600/322 |
| 6,415,236 B2 | * | 7/2002 | Kobayashi et al. ............ | 600/322 |
| 6,510,331 B1 | * | 1/2003 | Williams et al. .............. | 600/323 |

FOREIGN PATENT DOCUMENTS

| JP | 7-222736 | 2/1994 |
|---|---|---|
| JP | 9-019480 | 7/1995 |
| JP | 9-098972 | 10/1995 |

OTHER PUBLICATIONS

Atsushi Maki, Yuichi Yamashita, Yoshitoshi Ito, Eiju Watanabe, Yoshiaki Mayanagi and Hideaki Koizumi, "Spatial and Temporal Analysis of Human Motor Activity Using Noninvasive NIR Topography", Medical Physics, vol. 22, No. 12, Dec. 1995, pp. 1997–2005.

Yuichi Yamashita, Atsushi Maki and Hideaki Koizumi, "Wavelength Dependence of the Precision of Noninvasive Optical Measurement of Oxy–, Deoxy–, and Total–Hemoglobin Concentration", Medical Physics, vol.. 28, No. 6, Jun. 2001, pp. 1108–1114.

* cited by examiner

*Primary Examiner*—Eric F. Winakur
*Assistant Examiner*—Matthew Kremer
(74) *Attorney, Agent, or Firm*—Reed Smith LLP; Stanley P. Fisher, Esq.; Jean Carlos A. Marquez, Esq.

(57) ABSTRACT

The invention provides optical technique for measuring metabolism in a living body that can further reduce an error in measurement even if distance between irradiation and detection is fixed. The living body is classified into measurement regions and different measuring wavelengths are set according to the classification. For example, the head is classified into four regions of a parietal region, a frontal region, a temporal region and an occipital region and a wavelength according to each tissue is set in a wavelength selecting system. In measurement, wavelengths according to each measurement region are selected by multiple wavelengths-light radiating means. Besides, for a region having large personal difference, premeasurement is made using plural combinations of wavelengths and wavelengths are selected using a calculated error in measurement as a criterion.

7 Claims, 17 Drawing Sheets

○ : INCIDENT POSITIONS
● : DETECTION POSITIONS
▨ : MEASUREMENT POSITIONS

OPTICAL SYSTEM FOR MEASURING METABOLISM IN A BODY

BACKGROUND OF THE INVENTION

1. Field of the Invention

The present invention relates to technique for optical measurement, particularly relates to technique for measuring the information of the inside of a living body using light.

2. Description of the Related Art

Living body measuring technique using near infrared rays is applied to the measurement of a brain function. In Japanese Patent Application Laid-Open No. 9-098972, technique for simultaneously measuring a brain function at multiple points using rays of two wavelengths is disclosed and is used for measuring technique for imaging a brain function.

As shown in FIG. 2, the intensity change of transmitted light is measured by detecting light 2-1 radiated from the upside of a head skin 2-3 as detected light 2-2 at an apart point again. Based upon the change, the change of the concentration of hemoglobin in a brain cortex 2-5 between the radiated point and the detected point can be calculated. A reference number 2-4 in FIG. 2 denotes a skull and 2-6 denotes a measured middle part. Hemoglobin is classified into oxygenated hemoglobin and deoxidized hemoglobin depending upon an oxygenated state, however, as shown in FIG. 3, as respective absorption spectrums (absorption coefficients) 3-1, 3-2 are different, the change in the concentration of each hemoglobin can be independently measured by using rays of different two wavelengths. Heretofore, wavelengths of 780 nm (3-3) and 830 nm (3-4) have been often used.

An expression for calculating the change in each concentration of oxygenated hemoglobin and deoxidized hemoglobin is disclosed in Japanese Patent Application Laid-Open No. 9-098972 and on pages 1997 to 2005 of Medical Physics, 1995 No. 22 for example. As a blood oxidized state locally changes as a brain is activated, the change in each concentration of oxygenated hemoglobin and deoxidized hemoglobin is used for one of indexes showing the activity of a nerve.

It is disclosed on pages 1108 to 1114 of Medical Physics, 2001 No. 28 vol. 6 that in the method of measuring metabolism in a living body, the degree of an error varies depending upon a measuring wavelength. On the pages, an error of measurement in case a wavelength combined with 830 nm is shorter than conventional 780 nm in measurement in which distance (30 mm) between irradiation and detection is fixed is discussed. When a wavelength of 780 nm is made shorter in case it is supposed that the intensity of transmitted light and the magnitude of noise included in the intensity of transmitted light do not depend upon a wavelength, an absorption coefficient for deoxidized hemoglobin is increased and an error of the change in the concentration of hemoglobin in measurement is reduced. FIG. 4 shows the dependency theoretically shown of an error in measurement upon a wavelength. The x-axis shows the other measuring wavelength in case one measuring wavelength is fixed to 830 nm and the y-axis shows an error in measurement (the amplitude of noise). A reference number 4-3 denotes a wavelength of 780 nm often used heretofore. In FIG. 4, on the supposition that the magnitude of noise included in an original signal (a transmitted light signal) is fixed in each wavelength, an error in measurement (shown by a dotted line 4-1) of oxygenated hemoglobin and an error in measurement (shown by a full line 4-2) of deoxidized hemoglobin are shown. The validity of the theoretical prediction is verified in the measurement of a parietal region (the number of a living body=1).

As described above, a tendency that an error in measurement is reduced by using light of a shorter wavelength than 780 nm which has been often used in conventional type measurement equipment is known.

A method of selecting a wavelength suitable for measuring metabolism in a body is disclosed in Japanese Patent Application Laid-Open No. 7-222736 for example. In the patent application, a method of selecting a wavelength based upon a method of measuring not reflected light but light transmitted in a body and in consideration of the size of an object to be measured, that is, distance between irradiation and detection is proposed. For a condition to be a selection criterion, there are the following two conditions of a condition for precisely measuring an oxygenated state of hemoglobin and a condition for acquiring full transmitted luminous energy.

1) In case light of a wavelength in which difference between the absorbed amount of oxygenated hemoglobin and that of deoxidized hemoglobin is large is used, the change of an oxygenated state of hemoglobin can be precisely detected. Therefore, short wavelengths of approximately 600 nm are suitable.

2) To detect full transmitted luminous energy, a wavelength having high light transmittance in a body is required. Therefore, long wavelengths of the latter half of 700 nm to 900 nm are suitable.

As wavelengths that meet each condition described above are different, a method of selecting an optimum wavelength according to distance between irradiation and detection which is one cause which varies transmitted luminous energy in consideration of both conditions is disclosed in the above patent application.

In a method of measuring information inside a body using reflected light, measurement in the same depth is required and in addition, in case plural measurement points are set and imaging is required, a measuring method in which distance between irradiation and detection is fixed is adopted. Therefore, in prior art in which a wavelength was selected according to the variation of distance between irradiation and detection, a fixed measuring wavelength was always used.

However, as a result of measuring various regions, a wavelength suitable for reducing an error in measurement is different in regions different in a tissue even in measurement in case distance between irradiation and detection is the same. In case a shorter wavelength is used for a wavelength combined with 830 nm, an error in measurement is gradually reduced up to a wavelength of a certain value, however, an error increases from the wavelength of the certain value.

It is known that for example, the tissues of a body represented by a bone and a skin have different optical properties (an absorption coefficient and a light scattering coefficient). In the human head, the thickness of a bone, a skin and a muscle is different depending upon a region and an optical property is different every region. Therefore, a method of selecting a wavelength according to distance between irradiation and detection has a problem that a precise signal cannot be acquired.

SUMMARY OF THE INVENTION

Then, the object of the invention is to provide optical technique for measuring metabolism in a body that enables the further reduction of an error in measurement even if distance between irradiation and detection is fixed.

To achieve the object, in the invention, a light source of a wavelength according to the tissue in a measurement region of a living body and an optical property is selected out of plural light sources having different wavelengths. Or a wavelength variable light source that can radiate an arbitrary wavelength is provided and a wavelength according to the tissue of a measurement region of a living body and an optical property is selected.

FIG. 1 shows the basic concept of the invention. A measurement region of a living body is classified and different measuring wavelengths are set according to the classification. To explain the head of a living body for an example, the head is classified into four regions of a parietal region 1-1, a frontal region 1-2, a temporal region 1-3 and an occipital region 1-4 and wavelengths according to respective tissues are set in a wavelengths selection system 1-6. In measurement, a wavelength according to each measurement region is selected by multiple wavelengths light radiation means 1-5.

Light of a selected wavelength is modulated by a predetermined frequency for each position so that a signal can be separated according to plural measurement points and is sent to respective optical couplers. In each optical coupler, the modulated light is mixed with a light signal of a different wavelength and is sent to an optical fiber for radiation. The mixed wavelength shall be a wavelength selected out of plural light sources having different wavelengths or a wavelength selected by a wavelength variable light source or a fixed wavelength radiated from a fixed light source.

The mixed light from the optical fiber for radiation is radiated on the living body and a transmitted light signal from the living body is detected by an optical fiber for detection. After the detected light signal is converted to an electric signal, a signal is detected using a modulation frequency for the selected light signal by a demodulator. These signals are recorded and the change of the concentration of hemoglobin is calculated. Based upon the change, an image showing the activity of a brain is acquired.

In case a wavelength is to be set more precisely, it may be also determined in consideration of other characteristics of a body such as race, age and the distinction of sex.

Besides, in the invention, before real measurement, premeasurement is made using plural light sources having different wavelengths, an error for the variation of the concentration of hemoglobin is calculated and a wavelength is selected based upon the error. From a viewpoint of transmittance for a body, a wavelength of 600 to 900 nm is used for the premeasurement.

In case premeasurement is made at plural measurement points, light is modulated by a predetermined frequency according to each measurement point and is sent to an optical coupler. A mixed light signal is sent to an optical fiber for radiating light and is radiated on a measurement region. A light signal from the measurement region is detected by an optical fiber for detection and after the light signal is converted to an electric signal, a signal is detected utilizing a modulation frequency for the selected light signal by a demodulator. Based upon the detected light signal, the change in the concentration of hemoglobin in the combination of respective wavelengths and its error are calculated. A wavelength used in real measurement is selected by comparison in the magnitude of an error.

Light of a wavelength selected based upon the result of the premeasurement is modulated by a predetermined frequency in each position so that a signal can be separated according to plural measurement points and is sent to respective optical couplers. In each optical coupler, the modulated light is mixed with a light signal of a different wavelength and is sent to the optical fiber for radiation. The mixed wavelength shall be a selected wavelength out of plural light sources having different wavelengths or a wavelength selected by a wavelength variable light source or a fixed wavelength radiated from a fixed light source. Mixed light from the optical fiber for radiation is radiated on a body and the transmitted light signal from the body is detected by the optical fiber for detection. After the detected light signal is converted to an electric signal, a signal is detected using a modulation frequency for the selected light signal by the demodulator. These signals are recorded and the change in the concentration of hemoglobin is calculated. Based upon the change, an image showing the activity of a brain is acquired.

The effect of making the premeasurement before the real measurement is as follows. In the measurement using multiple wavelengths, as the quantity of data to be recorded and processed increases according to the number of wavelengths, the cost is increased. Therefore, the reduction of the cost can be realized by selecting used wavelengths based upon the result of the premeasurement for a short time and minimizing the number of wavelengths. To further reduce the cost, the premeasurement can be also made not at all measurement points but at only representative measurement positions.

A reason for selecting different wavelengths according to a measurement region of a body according to the invention will be described below.

It is found as a result of the measurement of various regions that a wavelength suitable for reducing an error in measurement is different depending upon a measurement region of a body. As a result of reviewing a wavelength which increases an error in measurement in a certain region, it is found out that the intensity of transmitted light is reduced and noise is increased. It is conceivable that as the absorption of all hemoglobin is increased by shortening a wavelength, the absorbed amount of light in a skin, a skull and a brain is increased and the detected intensity of transmitted light attenuates. As an amplification factor by a signal amplifier is increased according to the decrease of the intensity of transmitted light, noise made by the amplifier included in the detected intensity of transmitted light is also increased. That is, as noise included in the intensity of transmitted light is increased according to shortening a wavelength, an actual error in measurement has a tendency for a shorter wavelength to deviate more from a theoretical curve (shown in FIG. 4). Therefore, the final effect of the reduction of an error in measurement is determined by both a theoretical error in measurement determined by the absorption coefficient of each wavelength and noise included in the actual intensity of transmitted light different depending upon a measurement region.

As described above, it is found that even if distance between irradiation and detection is the same, a wavelength that reduces an error in measurement cannot be uniformly selected. In a conventional type method of setting a wavelength according to distance between irradiation and detection, only a fixed wavelength is used in case distance between irradiation and detection is the same. Therefore, even if a wavelength for which the reduction of an error in measurement is predicted based upon distance between irradiation and detection is used, noise included the intensity of transmitted light exceeds the effect of the reduction of an error in measurement predicted based upon its absorption coefficient and the error may increase. Conversely, in case noise included in the intensity of transmitted light is small, only a wavelength according to distance between irradiation and detection is selected even if a wavelength that further reduces an error in measurement can be used.

It is known that the tissue of a body represented by a bone and a skin has a different optical property (an absorption coefficient and a light scattering coefficient). It is found that the human head is different in the thickness of a bone, a skin and a muscle depending upon a region and an optical property is different every region. Therefore, even if light of the same wavelength is radiated, the intensity of transmitted light and noise included in the intensity of transmitted light are different depending upon a measurement region. As a wavelength suitable for reducing an error in measurement is different depending upon a measurement region, a method of selecting a wavelength in consideration of difference in a measurement region is required even if distance between irradiation and detection is fixed.

Besides, a personal error is large depending upon a measurement region and even if the same region is measured using the same wavelength, a case that an error is reduced and a case that an error is not reduced exist. In the Japanese Patent Application Laid-Open No. 7-222736, the method of measuring the intensity of transmitted light beforehand and selecting a used wavelength is disclosed, however, it is judged only whether measurement using the wavelength is possible based upon the intensity of transmitted light or not. As both the absorption coefficient into hemoglobin of a wavelength and the magnitude of noise included in the intensity of transmitted light have an effect upon an error in measuring the change of the concentration of hemoglobin to be measured, the evaluation of a wavelength based upon only the intensity of transmitted light is not sufficient.

Therefore, even if a used wavelength is a wavelength having the intensity of transmitted light judged to be insufficient for measurement, a case that the effect of the reduction of an error by an absorption coefficient is large and the precision of measurement is enhanced exists. In such a case, a method of selecting a wavelength in consideration of both the magnitude of noise included in a transmitted light intensity signal and an error in measurement predicted based upon the absorption coefficient of a measuring wavelength in addition to the intensity of transmitted light is important.

As described above, according to the invention, even if distance between irradiation and detection is fixed, measurement technique in which a wavelength according to each measurement region can be selected in consideration of difference in an optical property caused by the difference of a tissue is realized and besides, optical technique for measuring metabolism in a body in which a wavelength can be selected based upon an error in measuring the change in the concentration of hemoglobin to be measured is realized.

DETAILED DESCRIPTION OF THE PREFERRED EMBODIMENTS

Figure 1:
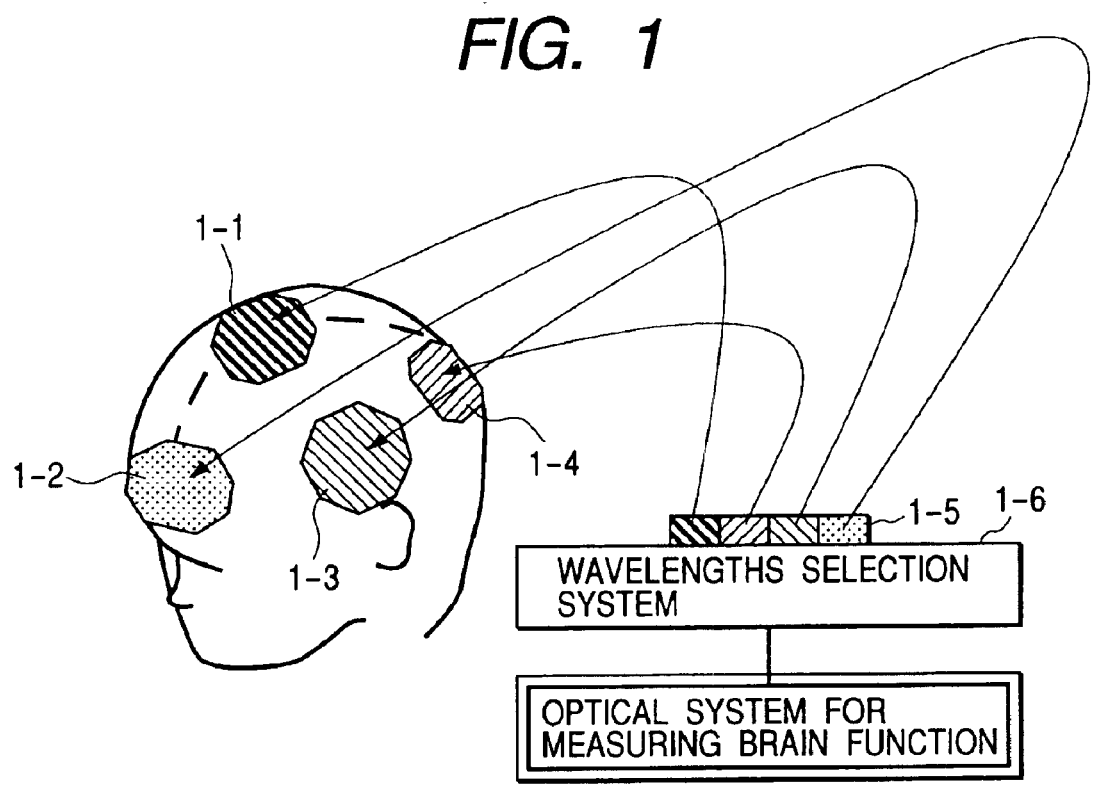
FIG. 1 shows a basic concept of the invention.
Figure 2:
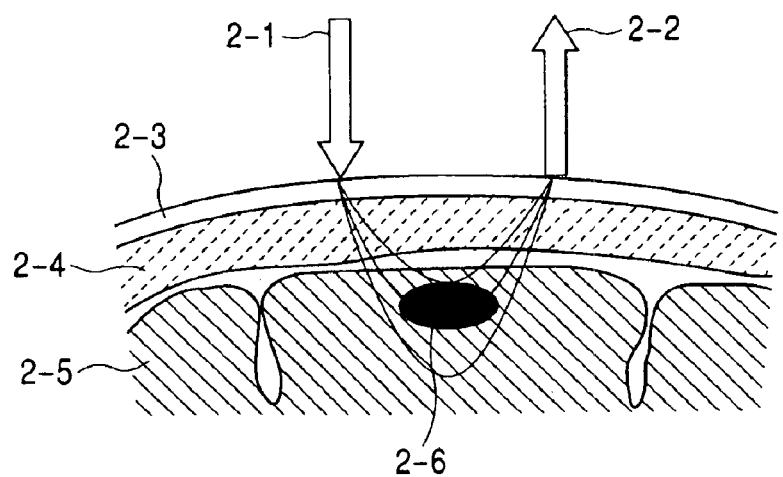
FIG. 2 is a schematic drawing showing the basic principle of brain function measuring technique using light.
Figure 3:
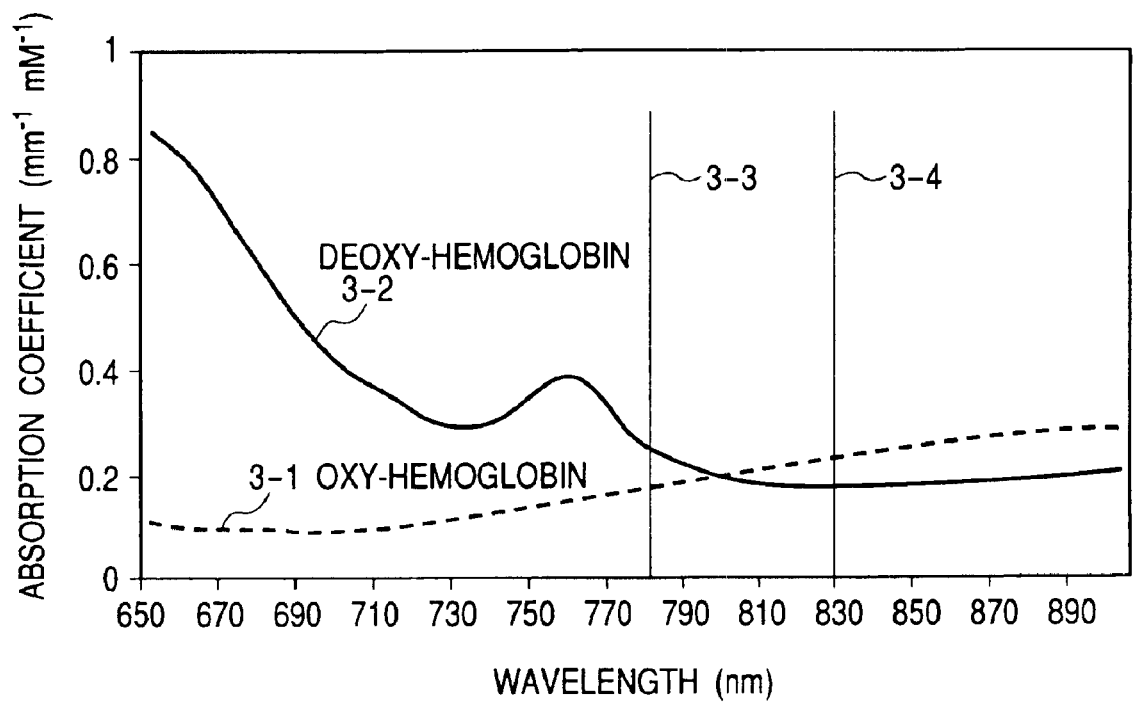
FIG. 3 shows each absorption spectrum of oxygenated hemoglobin and deoxidized hemoglobin and a measuring wavelength often used in an optical system for measuring metabolism in a body.
Figure 4:
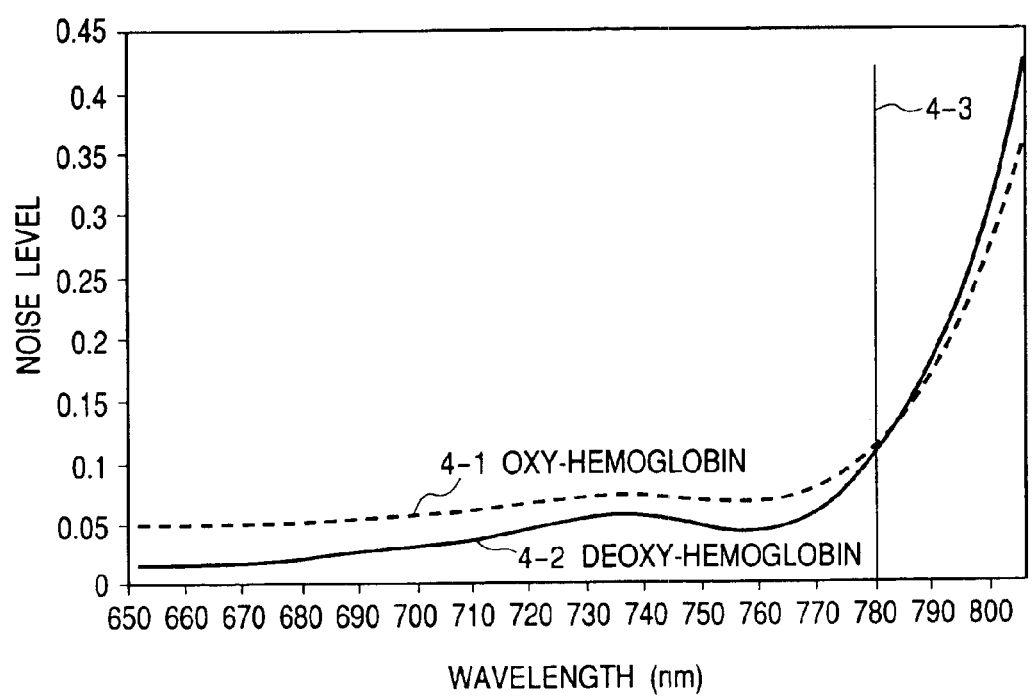
FIG. 4 shows the dependency theoretically acquired upon a wavelength of an error in measurement.

Referring to the drawings, embodiments of the invention will be described in detail below.

First Embodiment

A first embodiment of the invention will be described, referring to the configuration of a system shown in FIG. 5 below. The system equivalent to this embodiment is provided with a controller 5-3 formed by an electronic computer represented by a personal computer and a workstation, plural light sources different in a wavelength (in this embodiment, four light sources different in a wavelength 5-5 (678 nm), 5-6 (692 nm), 5-7 (780 nm) and 5-8 (830 nm) are provided), modulators 5-4 that modulate light from the plural light sources by different frequencies, a light selecting switch 5-9 controlled according to a transmitted signal from the controller 5-3 via a cable 5-10, an optical coupler 5-11 that couples light having one wavelength (in this embodiment, 830 nm from the light source 5-8) modulated by the modulator 5-4 and light having a wavelength selected by the optical switch 5-9, plural light radiating means for radiating light from the optical coupler 5-11 in different positions on a head skin of a living body 5-18 via an optical fiber for radiating light 5-13, plural optical fibers for detecting light 5-14 provided so that each end of which is located in a position apart by equal distance (in this embodiment, 30 mm) from each position in which light is radiated by the plural light radiating means, plural light receiving means formed by optical detectors 5-12 provided to respective optical fibers and a lock-in amplifier 5-1 to which a modulation frequency from the modulator 5-4 is input as a reference signal.

In this embodiment, plural light signals are detected at one point, however, a signal from any radiated position is differentiated by using the modulators. Except a method of separating plural light signals as described above, light signals can be also separated using pulse light without using the modulators at lighting timing.

Besides, only one wavelength is selected from the plural light sources, however, both wavelengths may be also selected from the plural light sources.

Figure 5:
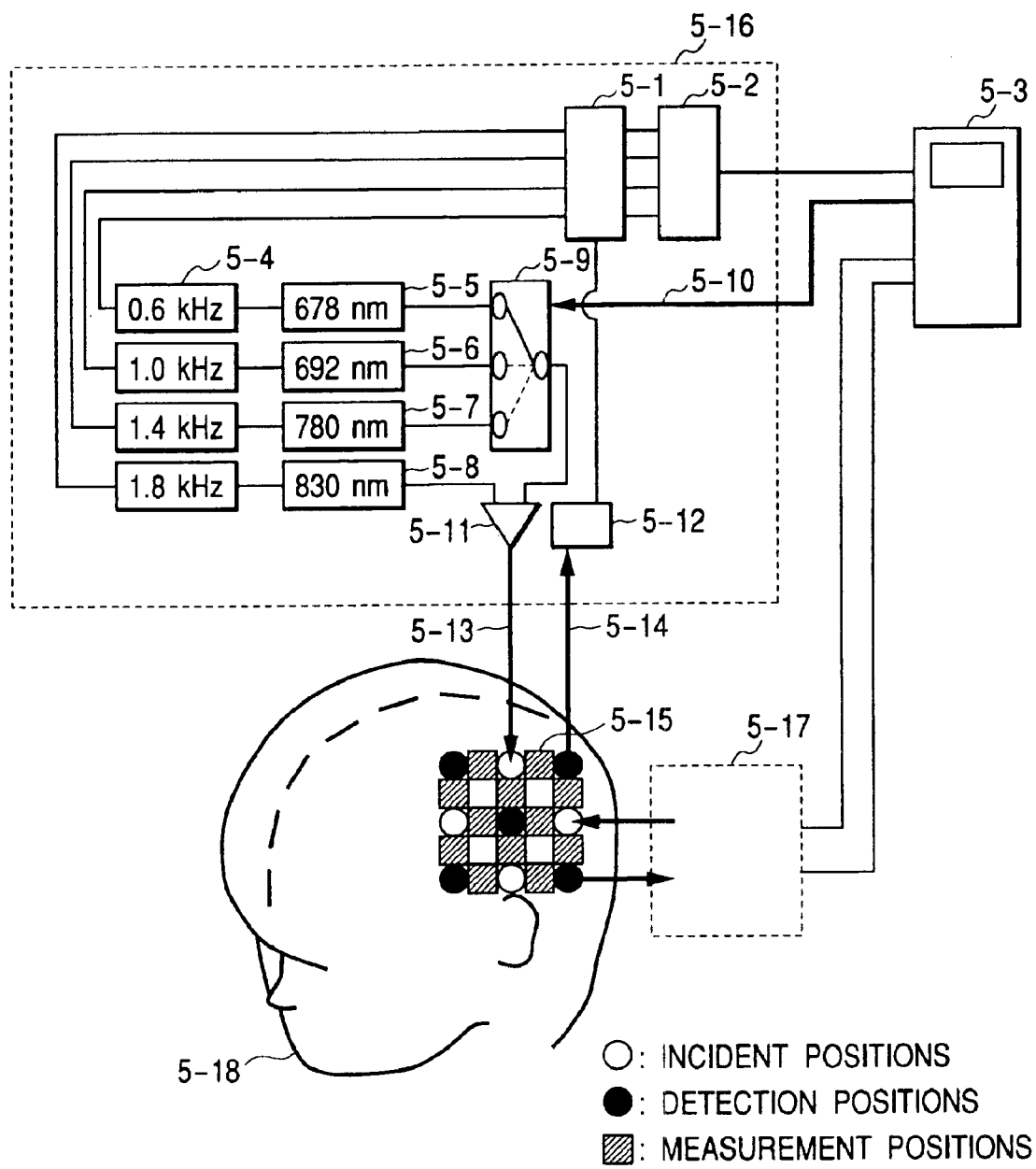
FIG. 5 explains the configuration of an optical system equivalent to a first embodiment of the invention.

In FIG. 5, a white circle (○) shown on the living body 5-18 denotes a light radiated position where the optical fiber for radiating light is arranged (in this embodiment, four locations), a black circle (●) denotes a light detected position where the optical fiber for detecting light is arranged (in this embodiment, five locations), and the light radiated position and the light detected position are alternately arranged. Each measurement position 5-15 is located at a substantial middle point between each light radiated position and the adjacent light detected position (in this embodiment, twelve locations).

In FIG. 5, only the configuration in one measurement position 5-15 of the system for measuring is shown in a frame 5-16, however, the configuration in another measurement position is also similar (for example, the contents of the frame 5-16 are the same as those of a frame 5-17).

Figure 6:
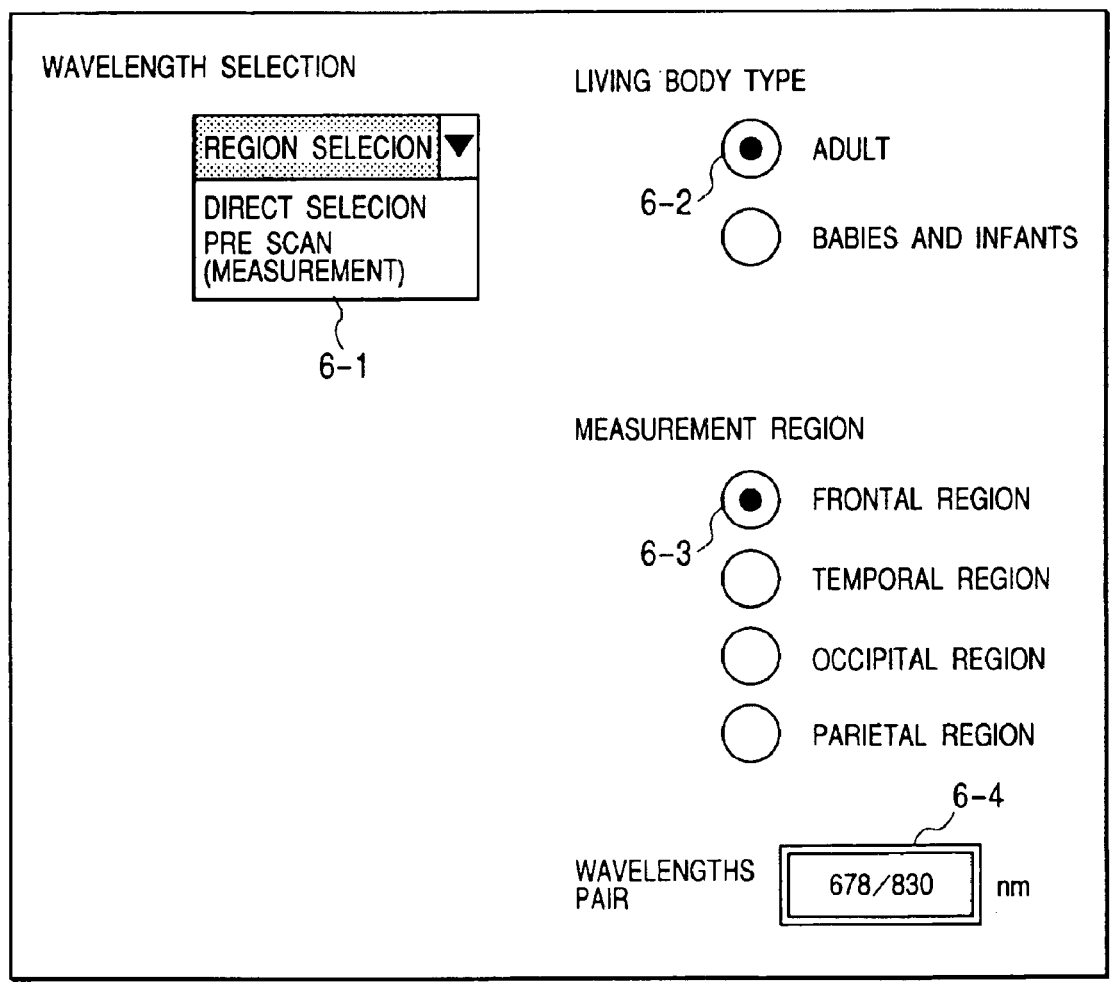
FIG. 6 shows an example of a wavelength selecting screen in the first embodiment of the invention.

In this embodiment, the living body is classified into regions and the controller selects the combination of wavelengths according to a region. FIG. 6 shows one example of an interface screen to be operated by an experimenter. When "Region Selection" is selected in a pull-down menu 6-1, radio buttons for setting living body type 6-2 and measurement region 6-3 are displayed. When the corresponding buttons are selected according to a living body type and a measurement region, optimum wavelengths for a measured object are selected according to a fixed rule and are displayed in a part 6-4 in which a wavelengths pair is displayed. For example, when "Adult" and "Temporal Region" are selected, "692/780 nm" is selected.

The rule for selection can be set based upon research to be a database using a magnetic resonance imaging method and can be arbitrarily set based upon the experiential knowledge of experimenters and the result of simulation. For the setting of the rule, there are both a case that only a developer of software can set the rule and a case that each user can arbitrarily set the rule.

Figure 7:
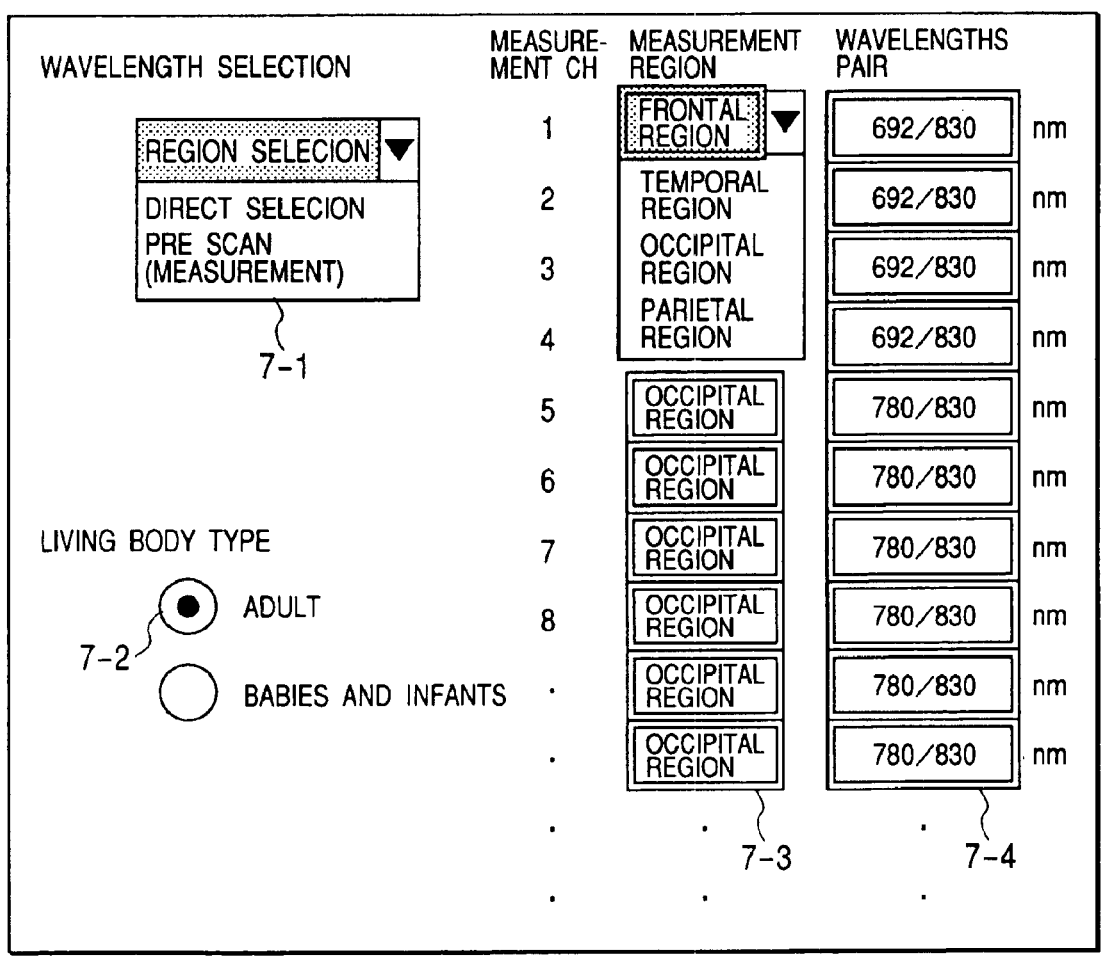
FIG. 7 shows another example of the wavelength selecting screen in the first embodiment of the invention.

As shown in FIG. 7, for example, "Region Selection" is selected in a pull-down menu 7-1, "Adult" is set by selecting a radio button 7-2, a measurement region is input every measurement channel in a pull-down menu 7-3 and suitable wavelengths can be also set in a display part 7-4. In case a large region to some extent is measured, different wavelengths are required to be set every measurement channel as shown in FIG. 7.

A wavelength determined by the controller is transmitted to the wavelength selecting switch 5-9 via the cable 5-10 and is selected there. After light of the wavelength is mixed with light 5-8 of 830 nm in the coupler 5-11, the mixed light is radiated on a predetermined light radiated position via the light radiating means 5-13. Light transmitted in the body transmitted from an adjacent light detected position via the fiber for detecting light 5-14 is converted to an electric signal by the optical detector 5-12. The optical detector is a device for detecting light reflected inside the living body and returned and converting it to an electric signal and for example, a photoelectric conversion device represented by an avalanche diode is used. The transmitted light signal converted to the electric signal by the optical detector is input to the lock-in amplifier 5-1.

As each optical detector 5-12 detects incident light from plural irradiation points located at equal distance from the detector and further, different two wavelengths are mixed in each incident light, the transmitted light signal is required to be separated every measurement position and every wavelength. As a modulation frequency from each modulator 5-4 is input to the lock-in amplifier 5-1 as a reference frequency, living body transmitted light intensity corresponding to an individual light source is separated and can be output.

After a separated transmitted signal of each wavelength which is output from the lock-in amplifier is converted from an analog signal to a digital signal in an A/D converter 5-2, it is input to the controller 5-3 and is stored there. The change in the concentration of hemoglobin in each measurement region is calculated based upon the transmitted light signals and is imaged.

A detailed signal processing process is disclosed in the Japanese Patent Application Laid-Open No. 9-98972 and on the pages 1997 to 2005 of No. 22 of Medical Physics, 1995.

As described above, in this embodiment, the measured object is classified into regions and wavelengths are selected in consideration of standard transmitted light intensity in each classification and a hemoglobin absorption coefficient of each wavelength. Therefore, a calculated error in measuring each change in the concentration of hemoglobin is reduced, compared with that in the conventional type.

Figure 8:
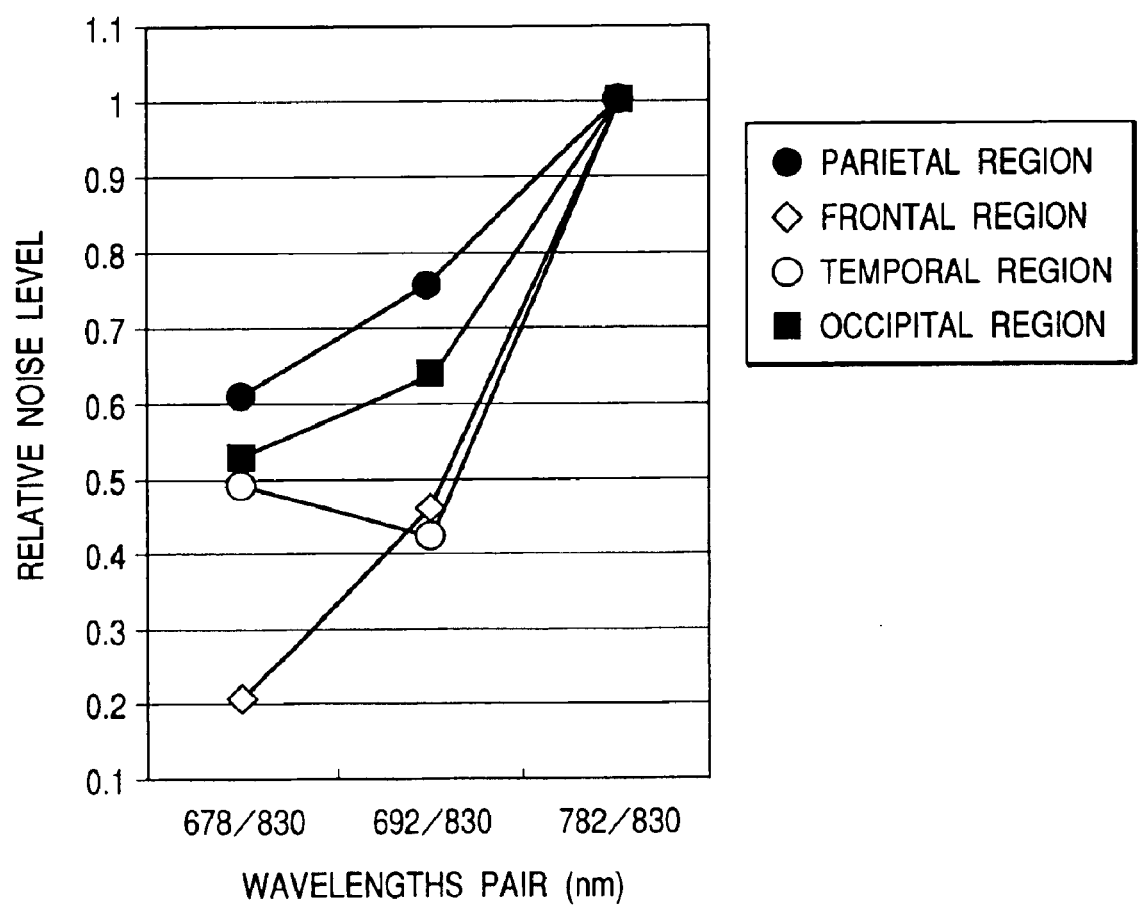
FIG. 8 shows difference depending upon a measuring wavelength in an error in measuring deoxidized hemoglobin as a result of measuring a representative living body.

FIG. 8 shows the effectiveness of this embodiment. In FIG. 8, the precision of measurement is evaluated by an error in measurement (the standard deviation of the change of hemoglobin in a state without a stimulus) and FIG. 8 shows the variation of the precision of measurement depending upon a measuring wavelength. In this case, imaging technique based upon simultaneous measurement at multiple points is presupposed and measurement size is set to 30 mm. In four measurement regions (the parietal region, the frontal region, the temporal region and the occipital region), measurement is made simultaneously using the combination of wavelengths (780/830 nm) often used heretofore and the combination of wavelengths (678/830 nm, 692/830 nm) in which the reduction of an error in measurement is theoretically predicted. In FIG. 8, assuming that an error in measuring deoxidized hemoglobin using wavelengths of 780 nm and 830 nm is 1, an error in measurement by each measurement wavelength is shown by a relative value.

As a result, in the parietal region, the frontal region and the occipital region, as a measuring wavelength becomes shorter, a tendency for an error in measurement to decrease is shown. However, for the temporal region, when the combination of wavelengths is 692/830 nm, an error is a minimum value and when the combination is 678/830 nm, an error conversely increases. This tendency is coincident in plural living bodies and it is conceivable that this tendency is one of typical patterns. Therefore, if it is set for a standard selection criterion that the combination of wavelengths of 678/830 nm is selected in the parietal region, the frontal region and the occipital region and the combination of wavelengths of 692/830 nm is selected in the temporal region, the precision of measurement is enhanced more than that in the conventional type that measuring wavelength of 780/830 nm are used.

When it is supposed that a group of living bodies shown in this embodiment are representative living bodies and a personal error is small, the selection criterion described above is completed. In case standard wavelengths for enhancing the precision of measurement are uniformly determined without using the system according to the invention, an optimum wavelength cannot be set depending upon a measurement region. For example, when the frontal region is selected as a criterion and the combination of wavelengths of 678/830 nm is adopted as the standard combination of wavelengths, an optimum wavelength cannot be used in measuring the temporal region. From such a viewpoint, the effectiveness of selecting a wavelength according to a measurement region is high.

As the example of the measurement described above is an example about the specific group of living bodies using the limit wavelengths, suitable wavelengths and the classification of measurement regions are not necessarily described above. As a wavelength that reduces an error in measurement depends upon the absorption coefficient of each measurement region, that is, the difference of a tissue, a case that a suitable selection criterion is different depending upon a group of living bodies, difference in a method of classifying measurement regions or difference between used wavelengths is conceivable. As a wavelength that reduces an error in measurement depends upon the intensity of transmitted light, a selection criterion also varies depending upon the intensity of radiated light itself.

The above example is important in that as a measuring wavelength that reduces an error in measurement is also different depending upon a measurement region in measurement at the same distance between irradiation and detection, the precision of measurement can be effectively enhanced by selecting a wavelength according to a measurement region.

Second Embodiment

A second embodiment of the invention is common to the first embodiment except a function for selecting a light source. Referring to the configuration of a system shown in FIG. 9, difference from the first embodiment will be described below.

In the system equivalent to this embodiment, no optical switch for selecting a wavelength is used. After light of plural wavelengths 9-5, 9-6, 9-7, 9-8 is coupled in a coupler 9-11, measurement is made as in the first embodiment. As a light signal of each wavelength is separated and is used for measurement, data by the combination of the plural wavelengths can be acquired after the measurement. Suitable data is selected every measurement position based upon the data. Or stabler data is acquired by using plural data and equalizing them.

Figure 9:
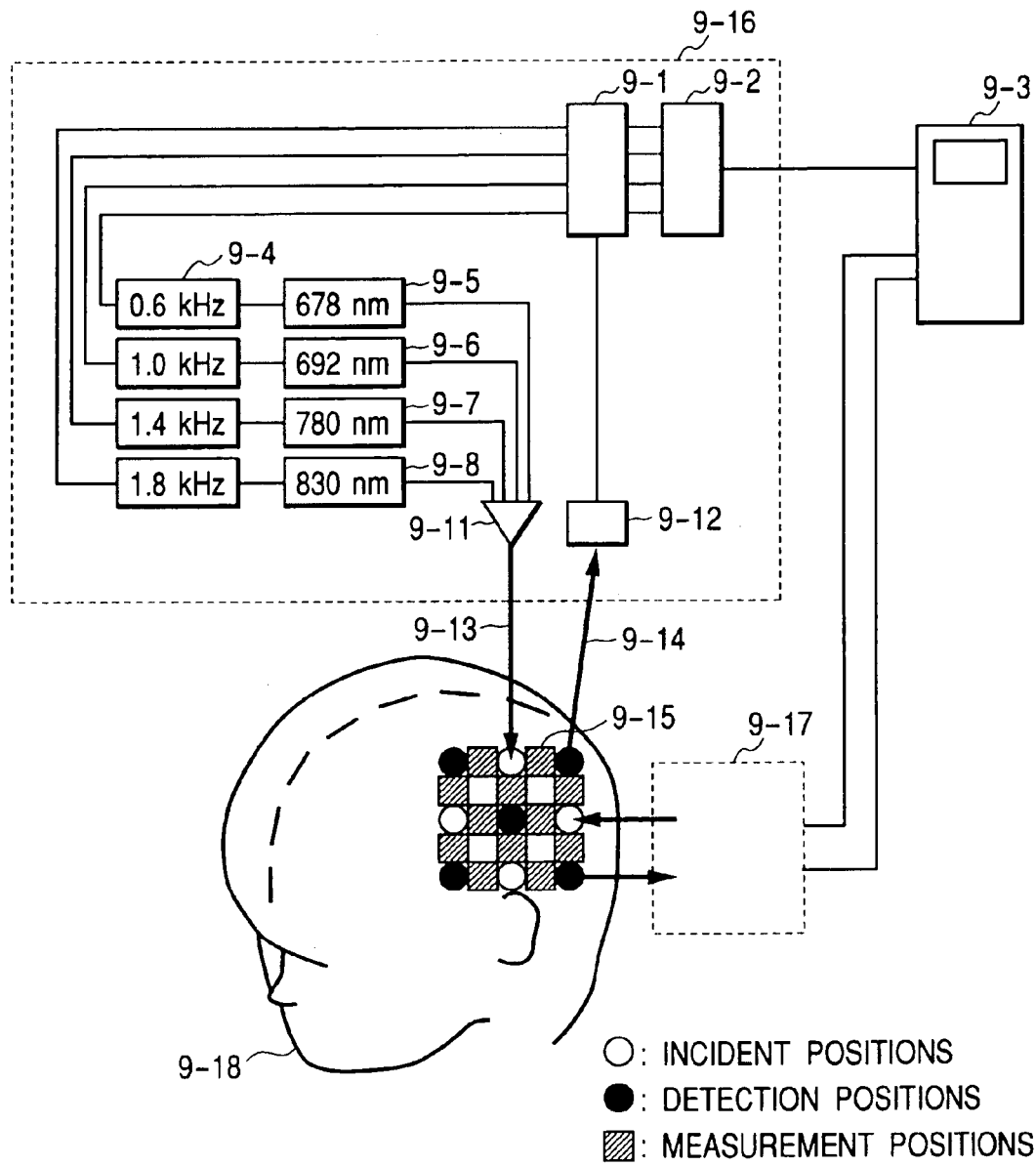
FIG. 9 explains the configuration of an optical system equivalent to a second embodiment of the invention.

In the system shown in FIG. 9, as all the combinations of wavelengths which are candidates are used for measurement without selecting wavelengths, wavelengths are not required to be selected beforehand. Therefore, a personal error which cannot be predicted based upon only a region can be verified after measurement. Besides, the stabilization of a signal using the data of the combination of plural wavelengths is enabled. In this embodiment, plural light signals are separated according to a measurement position by modulating the frequency of each light signal by a modulator, however, light signals can be also separated at lighting timing using pulse light without using the modulator.

Third Embodiment

A third embodiment of the invention is common to the first embodiment except a light source. Referring to the configuration of a system shown in FIG. 10, difference from the first embodiment will be described below.

A light source used in the system equivalent to this embodiment is a wavelength variable light source 10-5 that can vary a wavelength freely. When a measuring wavelength is determined by a controller 10-3 and an instruction from the controller is sent via a cable 10-10, the wavelength is set according to the instruction. Arbitrary wavelengths set by the two wavelength variable light sources 10-5 are coupled by a coupler 10-11 and measurement is made as in the first embodiment. Or two wavelengths of an arbitrary wavelength set by the wavelength variable light source and a specific wavelength of a fixed light source are coupled and measurement may be also made.

Figure 10:
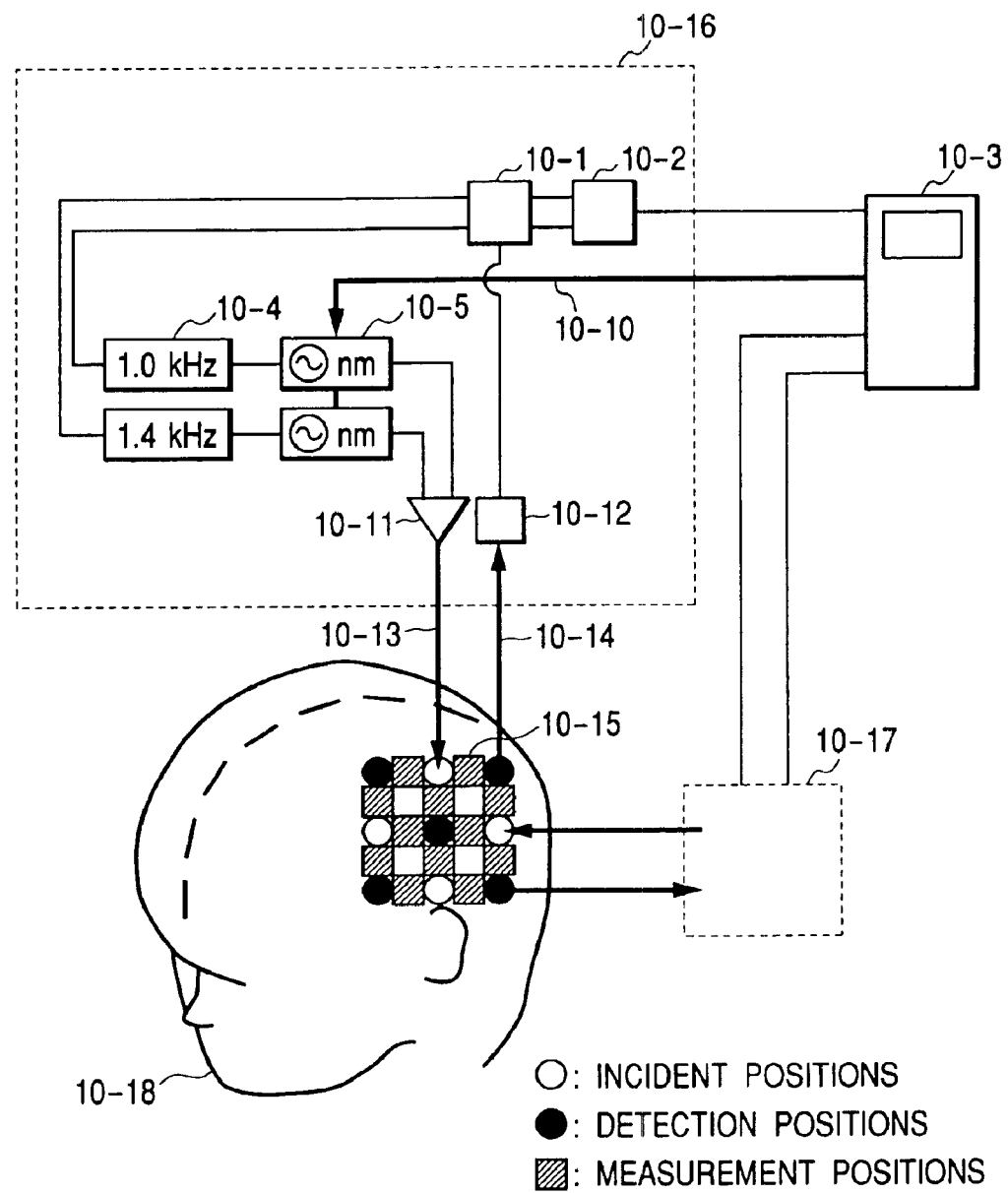
FIG. 10 explains the configuration of an optical system equivalent to a third embodiment of the invention.

In the system shown in FIG. 10, plural light signals are separated according to a measurement position by modulating the frequency of each light signal by a modulator. However, light signals can be also separated at lighting timing using pulse light without using the modulator.

The effect of this embodiment is common to that of the first embodiment, however, as wavelengths can be continuously varied and set, an error in measurement can be reduced close to a limit. Further, the measurement of living bodies of all generations and all race is enabled by one system.

Fourth Embodiment

A fourth embodiment of the invention is common to the first embodiment except a part of the configuration of a system and a method of setting a selected wavelength. Referring to the configuration of the system shown in FIG. 11, difference from the first embodiment will be described below.

Each light radiating means in this embodiment is provided with light sources of two wavelengths and the combination determined beforehand of wavelengths are radiated. For example, light radiated by light radiating means including an optical fiber 11-12 for radiating light is the mixed light of 692 nm and 830 nm, light radiated by light radiating means including an optical fiber for radiating light 11-14 is mixed light of 780 nm and 830 nm and light radiated by light radiating means including an optical fiber for radiating light 11-16 is the mixed light of 678 nm and 830 nm. Besides, corresponding to such light radiating means, light detecting means including optical fibers for detecting light 11-11, 11-13, 11-15 are provided. As described above, plural types of combinations of wavelengths can be used by using the configuration of the system in which each light radiating means can radiate light of different wavelengths.

As in the first embodiment, the combination of wavelengths is selected according to a measurement region. Differently in a concrete method of setting wavelengths from the first embodiment, the optical fiber for radiating light of wavelengths according to a measurement region is manually set. For example, the color of each optical fiber is differentiated depending upon radiated wavelengths and fiber fixtures (11-19, 11-20; 11-21, 11-22; 11-24, 11-25) on helmets 11-17, 11-23, 11-26 for each measurement region mounted on the head of a living body 11-18 are also colored by the same color as the optical fiber of corresponding wavelengths. When the differentiation of the selected optical fiber is facilitated as described above, the correct mounting of the optical fiber determined every measurement region is facilitated.

As described above, in this embodiment, the optical fiber that radiates wavelengths according to each measurement region is manually selected out of plural light radiating means that radiate light of different wavelengths. By this method, an error in measuring the change in the concentration of each hemoglobin can be reduced more as in the first embodiment than that in the conventional type method. As only two light sources are provided to one radiating means differently from the first embodiment, wavelengths are not required to be switched and measurement can be made at a small cost.

Fifth Embodiment

As the configuration of a system equivalent to a fifth embodiment of the invention and a general method of measuring are common to FIG. 5 referred in the first embodiment, they are omitted. A method of selecting wavelengths different from that in the first embodiment will be described below.

In this embodiment, the controller 5-3 judges and selects a wavelength that reduces an error in measurement most out of provided wavelengths. In the concrete, premeasurement is made using provided all wavelengths and the combination of wavelengths that reduce a calculated error in measuring the variation of the concentration of hemoglobin most is set in each measurement position.

Figure 12:
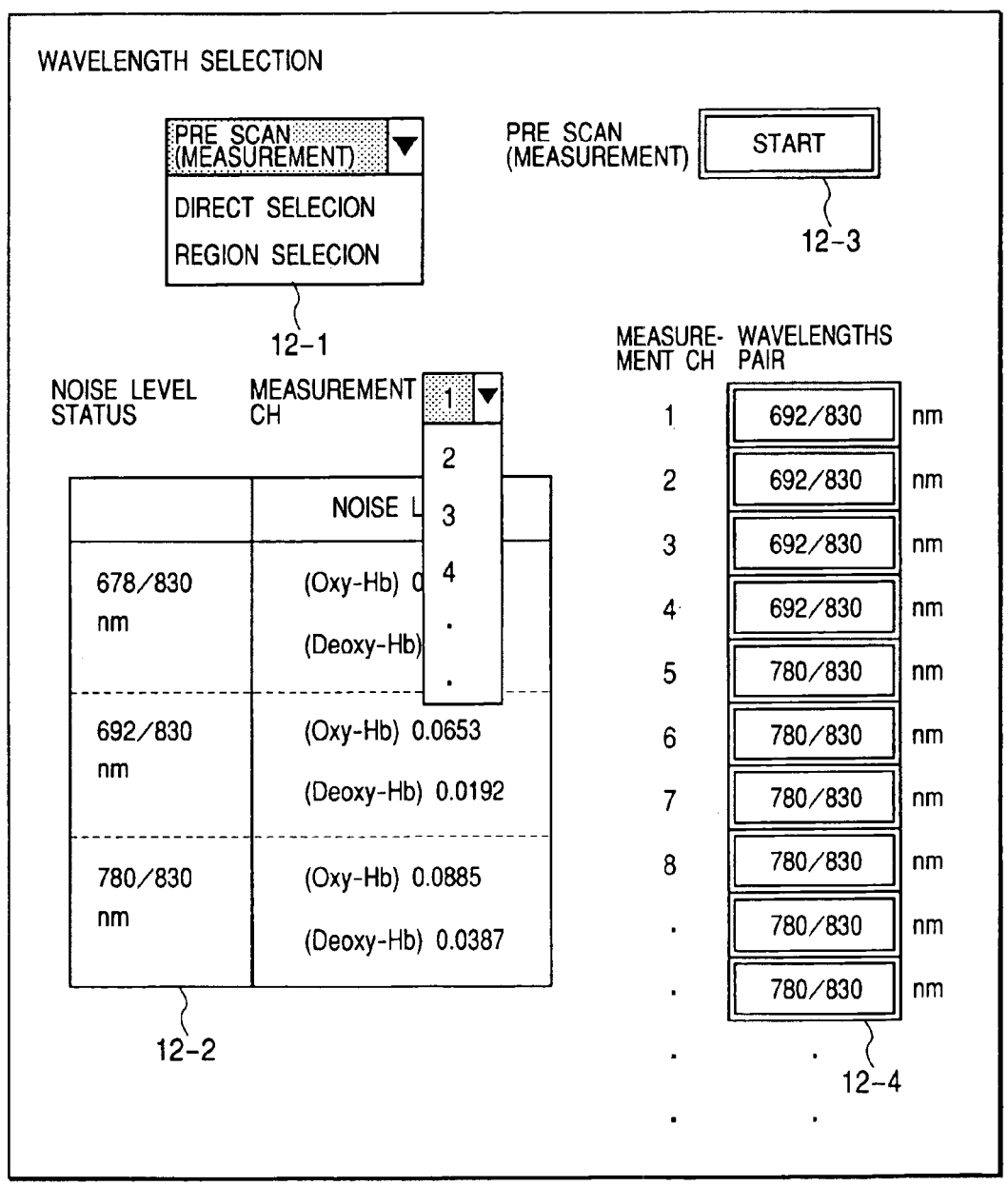
FIG. 12 shows a wavelength selecting screen equivalent to a fifth embodiment of the invention.

FIG. 12 shows an example of an interface screen operated by an operator of the controller. When "Premeasurement" is selected in a pull-down menu 12-1, a premeasurement start button 12-3 is displayed. When premeasurement is executed before measurement, the magnitude of an error in measurement in each combination of wavelengths is displayed in 12-2 and selected optimum wavelengths are displayed in 12-4.

The selected measuring wavelengths are set by the optical switch 5-9 and are radiated on each measurement region. As in this method, not the intensity itself of transmitted light but a calculated error in measuring the change in the concentration of hemoglobin is evaluated, comprehensive judgment in consideration of both of the attenuation of a transmitted light signal and the absorption coefficient of each wavelength is enabled. In case a suitable wavelength is not known and in case the region selecting method does not work out well, this method can be used for a search.

In case wavelengths are selected according to this method, the data of the classification of regions in the region selecting method shown in FIGS. 6 and 7 can be stored as a database by simultaneously inputting the classification of regions. The reliability of the region selecting method is continuously enhanced by utilizing the database for a selection criterion in the region selecting method. As in the first embodiment, the result of the premeasurement is also calculated every measurement channel and wavelengths suitable for each measurement channel can be selected.

Figure 14:
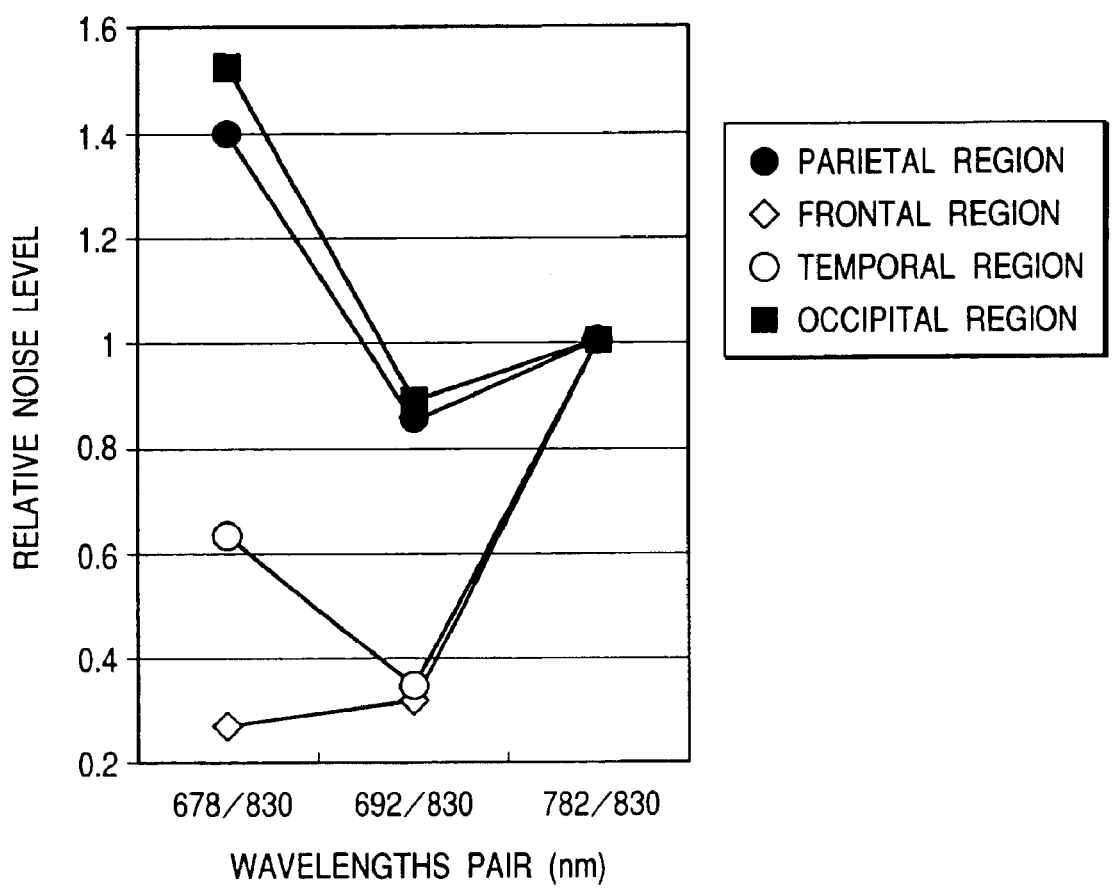
FIG. 14 shows difference depending upon a measuring wavelength in an error in measuring deoxidized hemoglobin as a result of measuring metabolism in a body having a different tendency from the representative living body.

The effect of this embodiment is shown in the examples of the measurement shown in FIGS. 8 and 14. The wavelength selecting method described in the first and second embodiments is effective in measurement regions in which the tendency of living bodies is coincident, however, as the tendency of living bodies is different depending upon a measurement region, there is a case that this embodiment is to be used. For example, in the parietal region and the occipital region of a living body shown in FIG. 14, an error in measurement using the combination of 678 nm and 830 nm is larger than that using the combination of 692 nm and 830 nm and the living body shows a tendency different from the living body shown in FIG. 9. As described above, in the parietal region and the occipital region in which the tendency of the wavelengths that reduce an error in measurement is different among living bodies, it is considered that the method of selecting measuring wavelengths based upon the result of the premeasurement is effective.

Differently from real measurement in which simultaneous measurement at multiple points is performed and measurement having duration according to an object is repeated, in premeasurement, measurement at multiple points is not required and measurement time is short. Therefore, compared with a method of measuring using multiple wavelengths in the real measurement, a method of limiting used wavelengths based upon the result of the premeasurement is more excellent in the cost. That is, as a small quantity of data has only to be recorded and processed, a burden on the controller is small.

When premeasurement is made, an error in measurement in the combination of each wavelength shown in FIGS. 8 and 14 is calculated without classifying an object of measurement depending upon a measurement region and the combination of wavelengths that reduce an error in measurement can be selected. Therefore, in case the living body shown in FIG. 8 is measured, the measuring wavelengths of 678 nm and 830 nm are selected for measurement in the parietal region, the frontal region and the occipital region and the measuring wavelengths of 692 nm and 830 nm are selected for measurement in the temporal region. In case the living body shown in FIG. 14 is measured, the measuring wavelengths of 678 nm and 830 nm are selected for measurement in the frontal region and the measuring wavelengths of 692 nm and 830 nm are selected for measurement in the parietal region, the temporal region and the occipital region. As described above, in a case to which the region selecting method cannot correspond, measuring wavelengths can be also set.

This selecting method is effective in most cases including a case that an object of measurement cannot be precisely classified and a case that wavelengths selected according to the region selecting method are not suitable. For example, suitable wavelengths can be selected in consideration of factors which are greatly different among individuals and which are difficult to know without actual measurement such as the thickness of a hairy root and the color of a skin.

Sixth Embodiment

A sixth embodiment of the invention is provided with light radiating/detecting means for premeasurement for determining wavelengths and plural pairs of light radiating means and light detecting means for real measurement respectively selectively used when the used combination of wavelengths is determined in the premeasurement.

Figure 13:
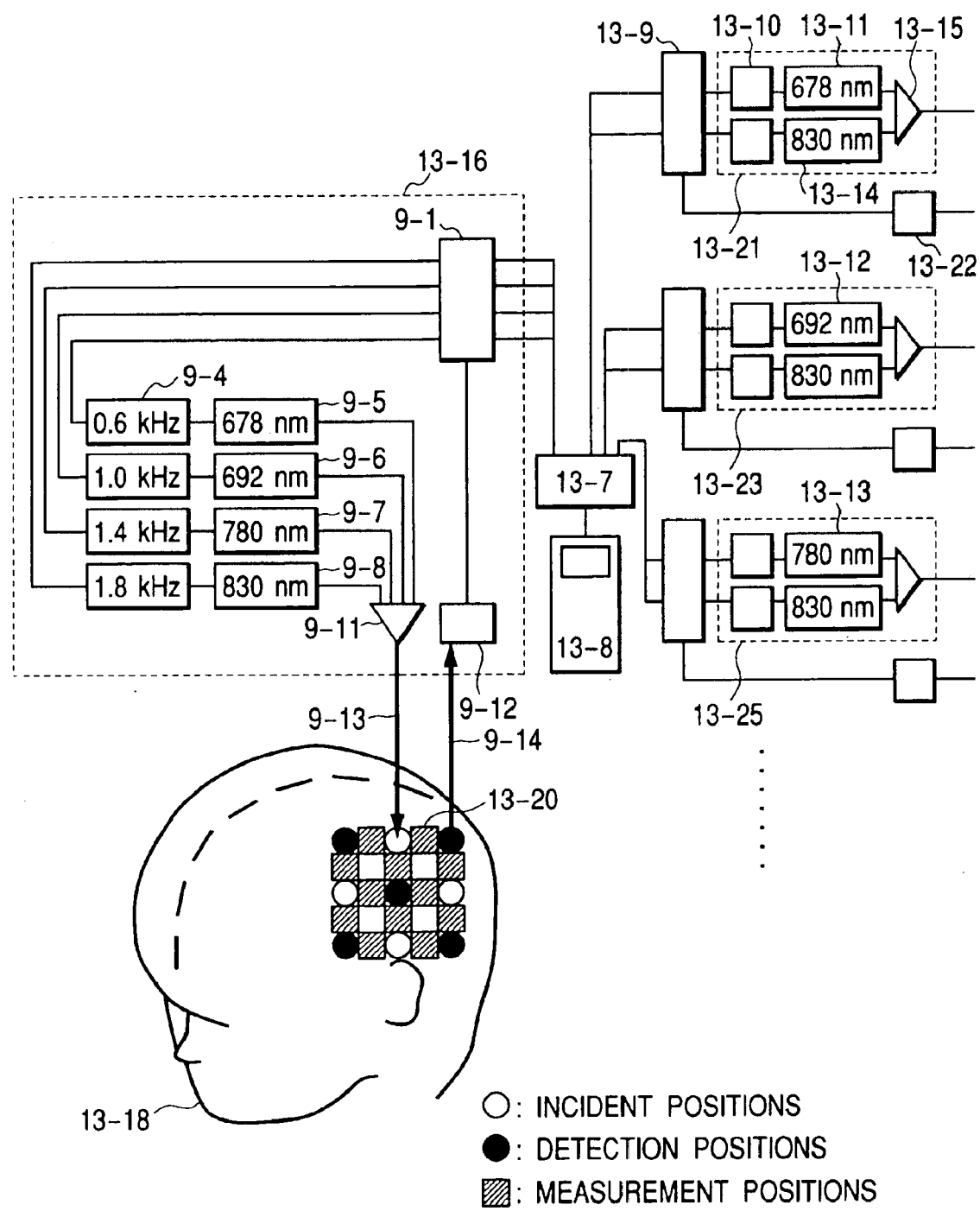
FIG. 13 explains the configuration of an optical system equivalent to a sixth embodiment of the invention.

FIG. 13 shows the configuration. The internal configuration of the light radiating/detecting means 13-16 for premeasurement is similar to that of the block 9-16 shown in FIG. 9 and the same reference number as that in FIG. 9 is allocated to the same part. The combination of wavelengths to be a candidate in this example is also the combinations of 678/830 nm, 692/830 nm and 780/830 nm. To make premeasurement using light of the combination of these wavelengths, plural light sources 9-5, 9-6, 9-7, 9-8 are provided and each light source is modulated by a different frequency depending upon each modulator 9-4. A signal detected by radiated light mixed by an optical coupler 9-11 and conducted to an incident position by an optical fiber for radiating light 9-13 is separated into a detection signal every wavelength in a lock-in amplifier 9-1. Separated each detection signal is received by a controller 13-8 via an A/D converter 13-7.

In this embodiment, as only one light radiating/detecting means 13-16 is provided for premeasurement, a representative measurement position 13-20 of a living body 13-18 is selected and premeasurement is made. A transformed type in which the number of optical detectors 9-12 is increased or further, the number of light radiating means for premeasurement is also increased, that is, a transformed type in which premeasurement can be made at plural measurement points is also possible. As in the fifth embodiment, an error in measurement in each combination of wavelengths is calculated based upon each signal detected by plural wavelengths and acquired in premeasurement and the combination of wavelengths that reduce an error in measurement most is selected.

In this embodiment, light radiating means for measurement dedicated to each combination of wavelengths to a candidate is provided. Light radiating means 13-21 for measurement using the wavelengths of 678 nm and 830 nm includes modulators 13-10, a light source 13-11 for the wavelength of 678 nm, a light source 13-14 for the wavelength of 830 nm and an optical coupler 13-15. Corresponding to the light radiating means, light detecting means including an optical detector 13-22 and a lock-in amplifier 13-9 is provided. Light radiating means 13-23 for measurement using the wavelengths of 692 nm and 830 nm and light radiating means 13-25 for measurement using the wavelengths of 780 nm and 830 nm are also similarly configured. However, a light source 13-12 is for radiating the wavelength of 692 nm and a light source 13-13 is for radiating the wavelength of 780 nm. Though the following light radiating means are not shown, light radiating means are provided by the number of incident positions every combination of wavelengths. Similarly, light detecting means are provided by the number of detection positions every combination of wavelengths and the output terminals of all lock-in amplifiers are connected to the controller 13-8 via the A/D converter 13-7.

When the combination of wavelengths in real measurement is determined by the premeasurement, the optical fiber fixed to a fiber fixture mounted on the living body 13-18 is connected to the corresponding light radiating means and the corresponding optical detector. Hereby, measurement by the selected combination of wavelengths is enabled.

In this embodiment, the number of special light radiating/detecting means for premeasurement provided with a function for mixing light of multiple wavelengths and a function for separating corresponding to the function may be small and the light radiating means for real measurement may be configured so that mixing two wavelengths and separating into two wavelengths are performed as in the conventional type. Therefore, this embodiment is advantageous in the cost of the system. Besides, the configuration of the light radiating means for real measurement is further transformed and light radiating means in which wavelengths can be selected can be also configured by the optical switch shown in FIG. 5. The number of light sources in the whole system is reduced by the transformation. As the selection of wavelengths is completed by operating the optical switch with the connection of the optical fiber fixed, there is an advantage that the operation of the system is simpler.

Seventh Embodiment

As the configuration of a system and a general measuring method in a seventh embodiment of the invention are common to those in the first embodiment, they are omitted. Only a wavelengths selecting method different from that in the first embodiment will be described below.

Figure 15:
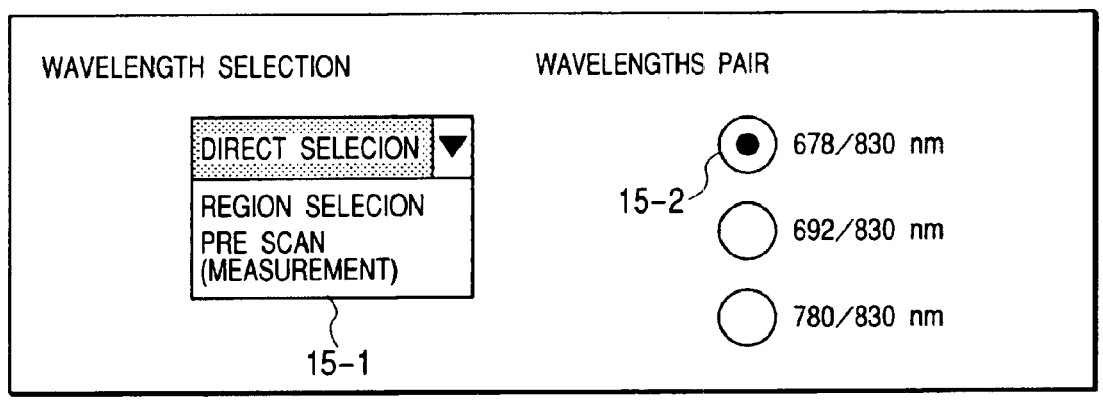
FIG. 15 shows an example of a wavelength selecting screen equivalent to a seventh embodiment of the invention.

In this embodiment, an operator directly selects arbitrary wavelengths out of the plural combinations of wavelengths to be a candidate. FIG. 15 shows an interface screen operated by the operator of a controller. When "Direct Selection" is selected in a pull-down menu 15-1, the selectable plural combinations of wavelengths are displayed. The corresponding combination of wavelength is adopted by clicking a radio button 15-2 located on the left side of the used combination of wavelengths.

Figure 16:
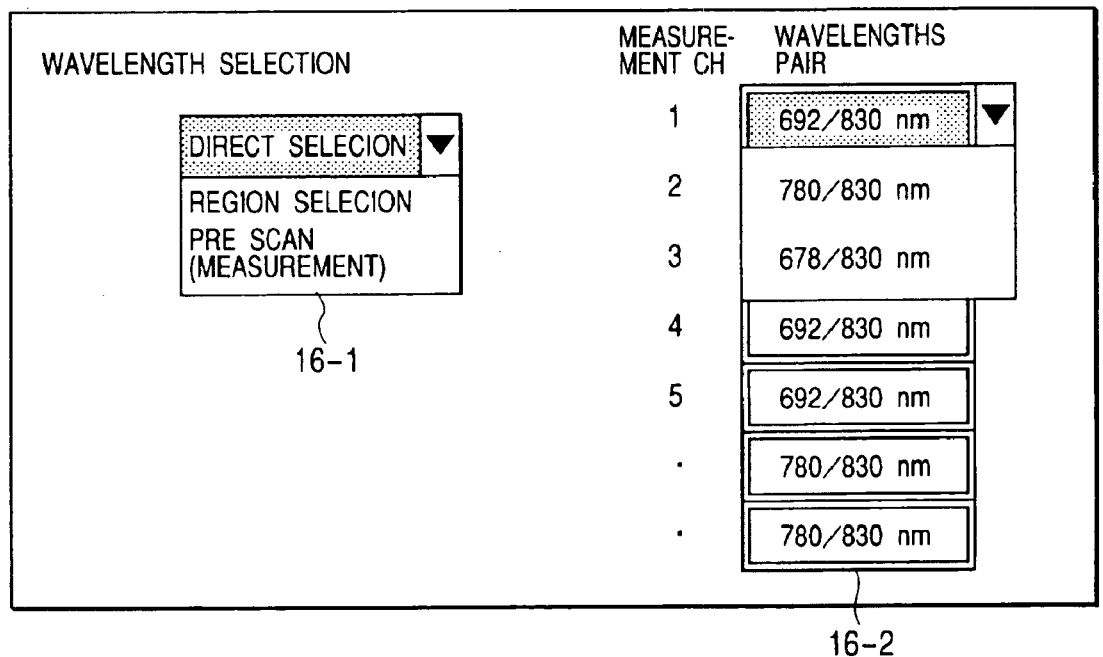
FIG. 16 shows another example of the wavelength selecting screen equivalent to the seventh embodiment of the invention.

As shown in FIG. 16, when "Direct Selection" is selected in a pull-down menu 16-1, measurement wavelengths are selected in a pull-down menu 16-2 every measurement channel and can be also set. As in the first embodiment, determined wavelengths are set by a wavelength selecting switch 5-9 and are coupled in a coupler 5-11. Or as in the third embodiment, suitable wavelengths are set by a wavelength variable light source 10-5 and are coupled in a coupler 10-7. This wavelengths selecting method is effective in case the selection of a region cannot be applied, in case suitable measuring wavelengths are known beforehand or in case specific measuring wavelengths are to be used for any reason.

Figure 11:
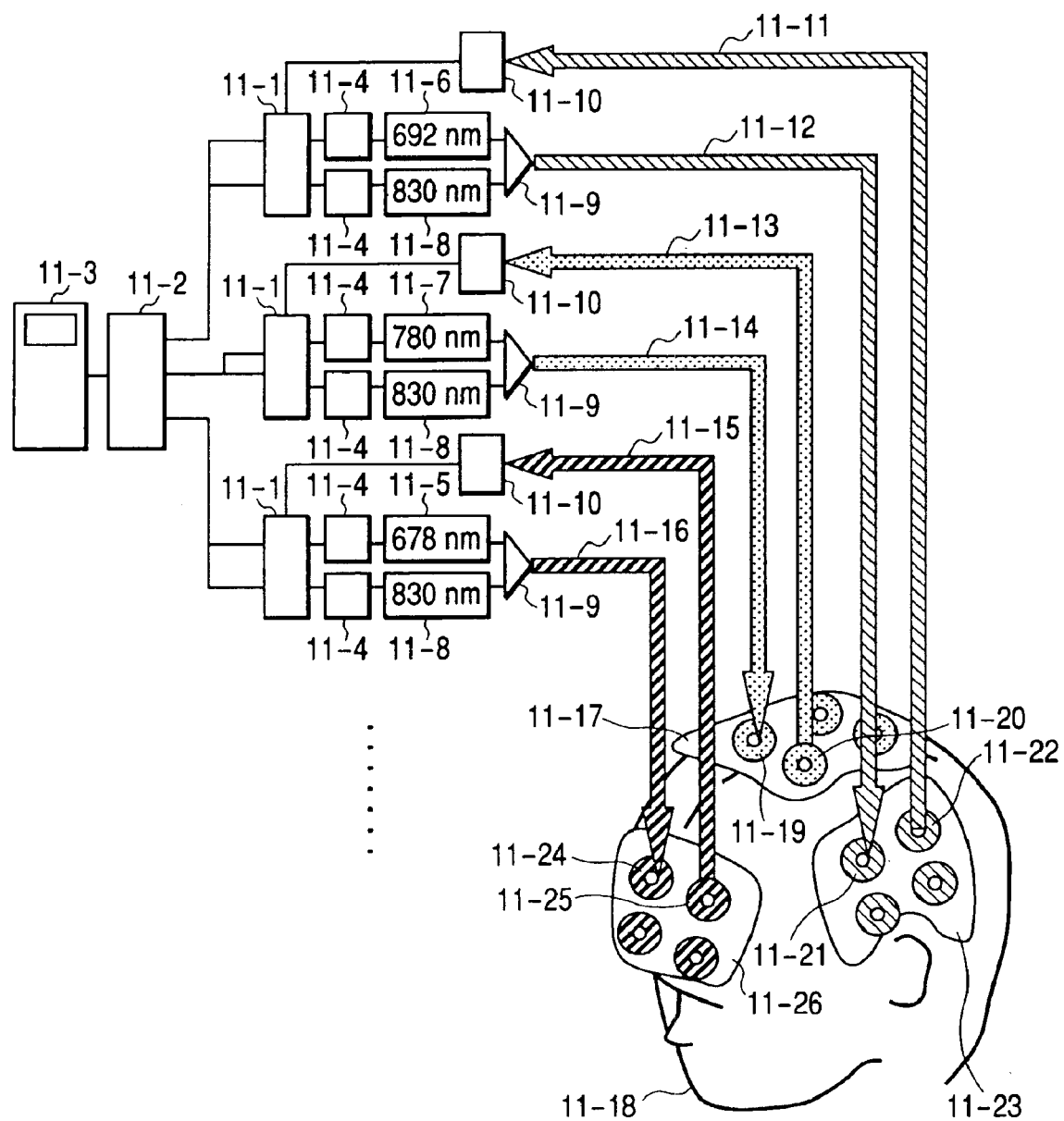
FIG. 11 explains the configuration of an optical system equivalent to a fourth embodiment of the invention.

In the configuration of the system provided with the plural types of light radiating means for radiating fixed wavelengths and the plural types of optical detectors respectively shown in FIGS. 11 and 13, arbitrary light radiating means can be also selected manually.

Figure 17:
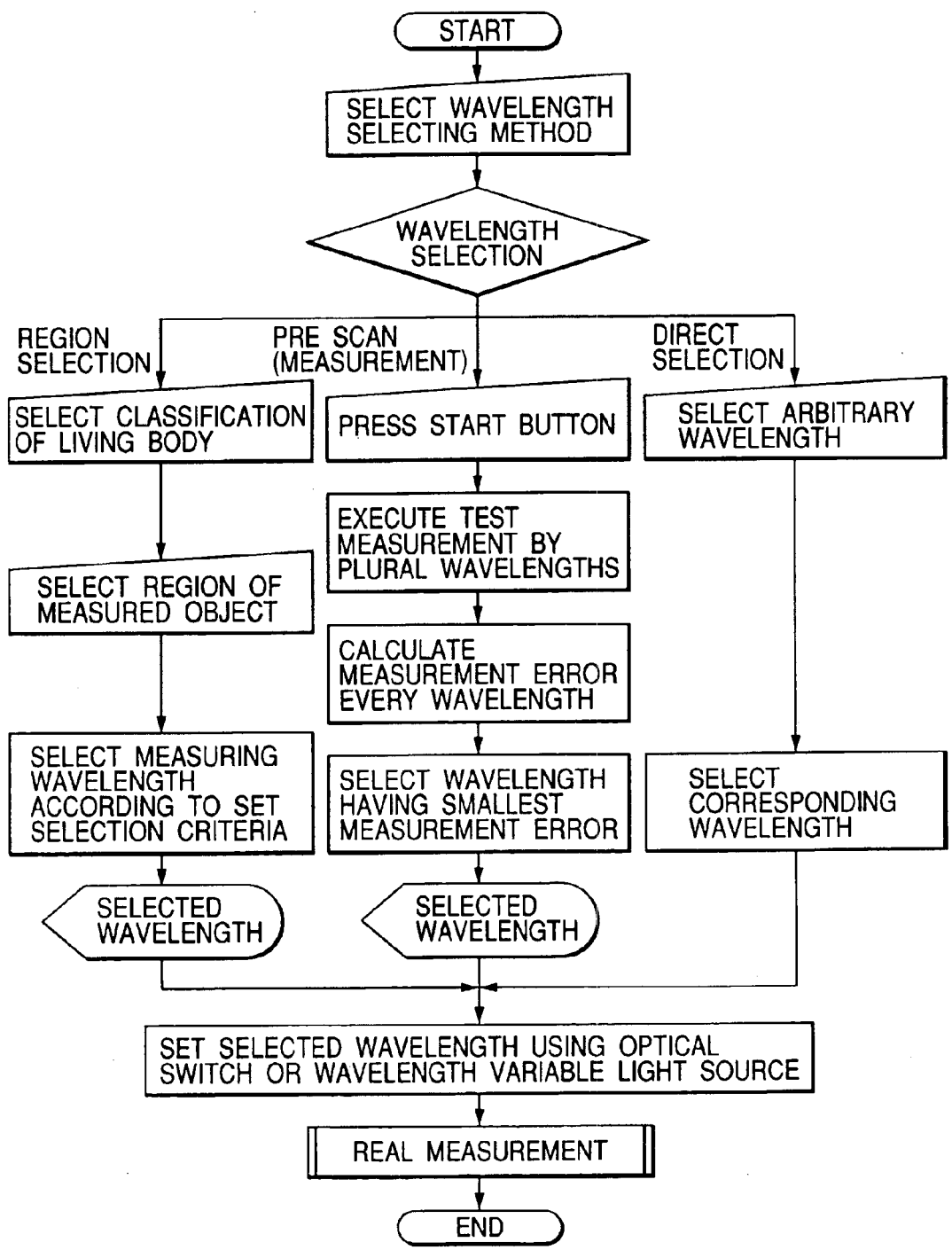
FIG. 17 shows a process for selecting a set wavelength in the embodiments of the invention.
Figure 18:
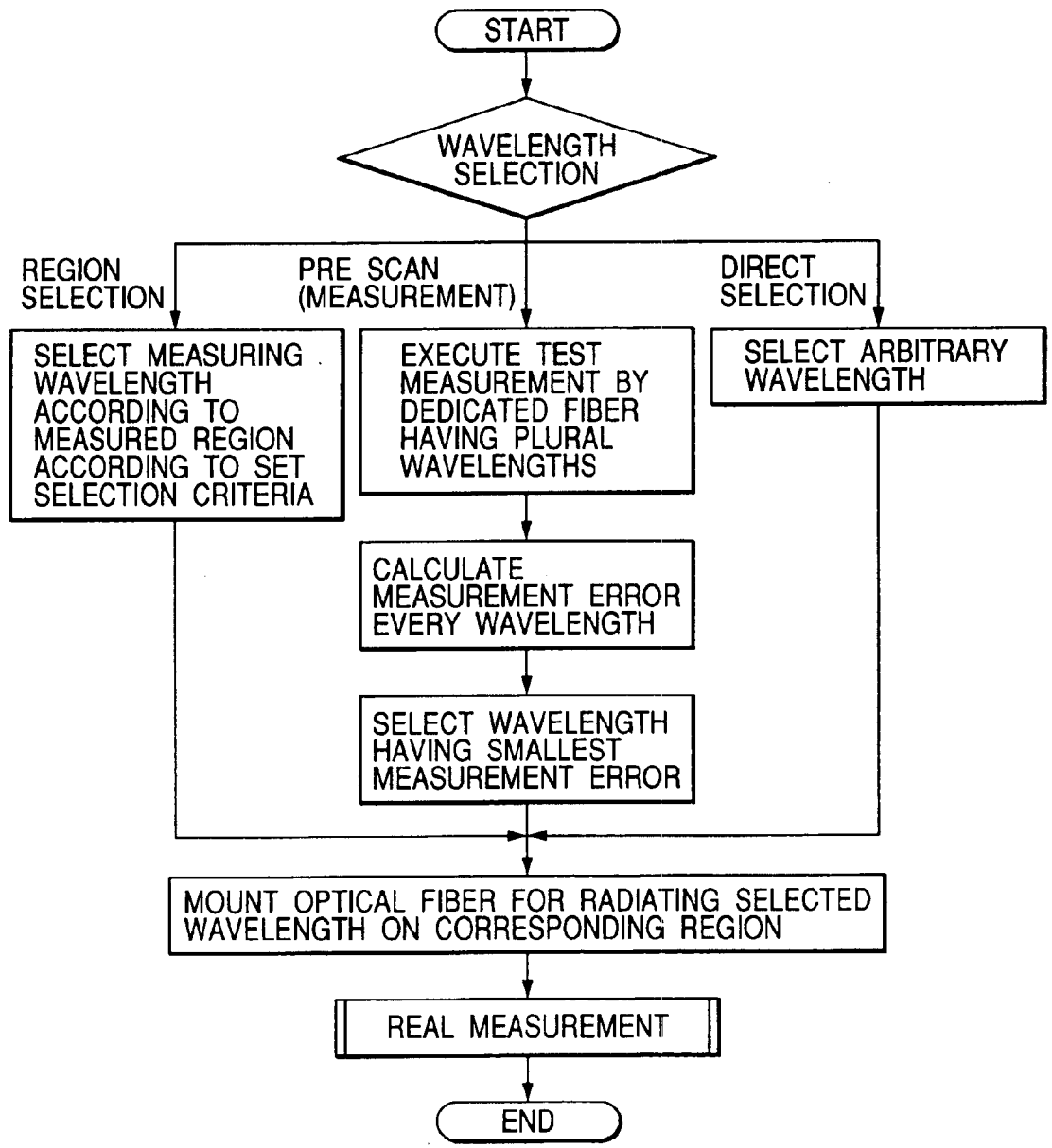
FIG. 18 shows another process for selecting a set wavelength in the embodiments of the invention.
Figure 19:
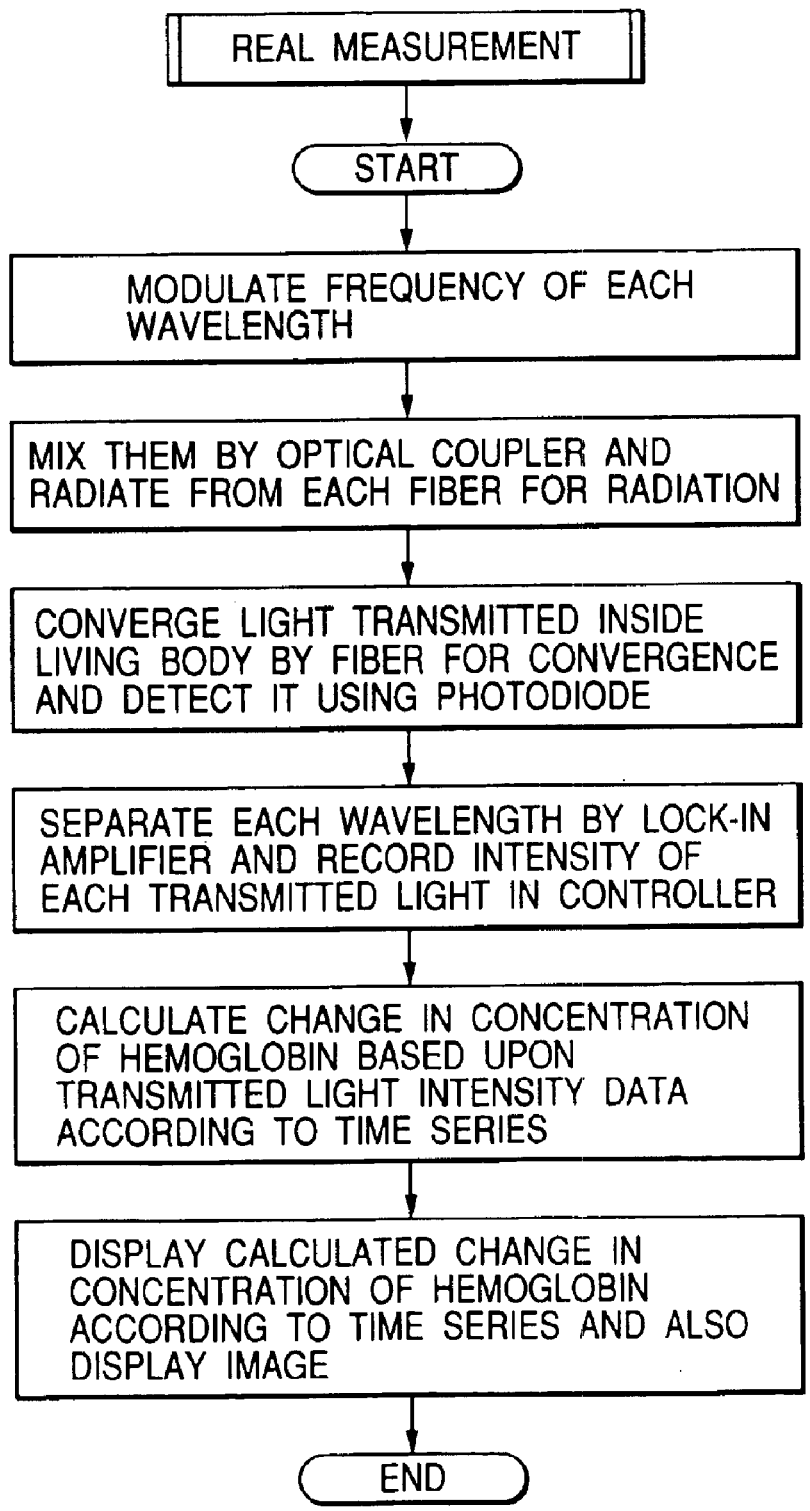
FIG. 19 shows a flow of main measurement after a wavelength is selected in the invention.

FIGS. 17, 18 and 19 are flowcharts showing each selection process of the wavelengths setting method in the embodiments described in detail above.

FIG. 17 is a flowchart showing wavelengths selection algorithm related to the first, second, third, fifth and seventh embodiments of the invention and shows a case that selected wavelengths are set by the controller.

FIG. 18 is a flowchart showing wavelengths selection algorithm related to the fourth, sixth and seventh embodiments of the invention and shows a case that selected wavelengths are set manually.

FIG. 19 shows the flow of real measurement after measuring wavelengths are set.

As described in detail above, according to the invention, as wavelengths can be set according to a measurement region in measuring metabolism in a living body and wavelengths can be set according to a final error in measurement depending upon noise included in a transmitted light signal in each measurement position and the absorption coefficient of hemoglobin, an error in measurement can be minimized. As the power of detecting a signal is enhanced, compared with the conventional type measuring method, the frequency of averaging required for removing the noise is reduced and effect such as the reduction of measurement time and the reduction of a load upon a living body is acquired. As wavelengths can be selected according to each measurement position in the system for imaging using simultaneous measurement at multiple points, particularly for measuring the whole brain, wavelengths can be selected so that the whole dispersion of an error is minimized. Signals in different measurement positions can be compared by equalizing S/N ratio at each measurement point.

The examples of the configuration included in the invention are as follows.

(1) The optical system for measuring metabolism in a body based upon an optical system for measuring metabolism in a body in which light radiating means for radiating light on the living body and light receiving means for detecting transmitted light radiated from the light radiating means and propagated in the living body are arranged on the living body and which is configured so that information in the living body is acquired based upon a signal detected by the light receiving means with a substantially middle point of the light radiating means and the light receiving means as a measurement point and characterized in that the light radiating means is provided with plural light sources respectively having a different wavelength and the light source having a wavelength according to the tissue of a measurement region in the living body and its optical property is selected out of the plural light sources.

(2) The optical system for measuring metabolism in a body based upon the optical system for measuring metabolism in a body described in above (1) and characterized in that for the selection of wavelengths, an object of measurement is classified into measurement regions and suitable wavelengths are selected out of wavelengths set beforehand every measurement region.

(3) The optical system for measuring metabolism in a body based upon the optical system for measuring metabolism in a body described in above (1) and characterized in that for the selection of wavelengths, premeasurement is made beforehand using plural measuring wavelengths, an error of a detected signal is calculated and wavelengths are selected based upon the error.

(4) The optical system for measuring metabolism in a body based upon the optical system for measuring metabolism in a body described in above (1) and characterized in that a display for displaying a wavelengths selecting method according to a preset criterion and according to an object of measurement is provided.

(5) The optical system for measuring metabolism in a body based upon the optical system for measuring metabolism in a body described in above (1) and characterized in that the light radiating means is provided with a wavelength variable light source that can radiate light of an arbitrary wavelength and wavelengths according to the tissue of a measurement region in the living body and its optical property can be selected by selecting any light source of the plural light sources and the wavelength variable light source.

(6) The optical system for measuring metabolism in a body based upon an optical system for measuring metabolism in a body in which light radiating means for radiating light on the living body and light receiving means for detecting transmitted light radiated from the light radiating means and propagated in the living body are arranged on the living body and which is configured so that information in the living body is acquired based upon a signal detected by the light receiving means with a substantially middle point of the light radiating means and the light receiving means as a measurement point and characterized in that the light radiating means is provided with a wavelength variable light source that can radiate light of an arbitrary wavelength and a wavelength of light radiated from the light source is selected according to the tissue of a measurement region in the living body and its optical property.

(7) The optical system for measuring metabolism in a body based upon the optical system for measuring metabolism in a body described in above (6) and characterized in that for the selection of wavelengths, an object of measurement is classified into measurement regions and suitable wavelengths are selected out of wavelengths preset every measurement region.

(8) The optical system for measuring metabolism in a body based upon the optical system for measuring metabolism in a body described in above (6) and characterized in that for the selection of wavelengths, premeasurement is made beforehand using plural measuring wavelengths, an error of a detected signal is calculated and wavelengths are selected based upon the error.

(9) The optical system for measuring metabolism in a body based upon the optical system for measuring metabolism in a body described in above (6) and characterized in that a display for displaying a wavelengths selecting method according to a preset criterion and according to an object of measurement is provided.

(10) The optical system for measuring metabolism in a body based upon the optical system for measuring metabolism in a body described in above (6) and characterized in that the light radiating means is provided with plural light sources respectively having a different wavelength and wavelengths according to the tissue of a measurement region in the living body and its optical property can be selected by selecting any light source of the wavelength variable light source and the plural light sources.

(11) The optical measuring method characterized in that a process for radiating light on a predetermined incident position of a living body, a process for detecting transmitted light propagated in the living body in a predetermined light receiving position and a process for acquiring information in the living body based upon a detected signal with a substantial middle position of the light incident position and the light receiving position respectively on the living body as a measurement point are provided, light is radiated on the living body using plural light sources that can radiate light of different wavelengths or a wavelength variable light source that can radiate light of an arbitrary wavelength and wavelengths according to the tissue of a measurement region in the living body and its optical property are selected from the plural light sources or the wavelength variable light source.

(12) The optical system for measuring metabolism in a body based upon an optical system for measuring information inside a living body using light and characterized in that wavelengths according to the optical property of a measurement region are selected according to difference in the tissue of the measurement region.

(13) The optical system for measuring metabolism in a body based upon an optical system for measuring metabolism in a body provided with plural light radiating means for radiating light of wavelengths from a visible region to a near infrared radiation region on the living body, plural light receiving means for detecting light transmitted inside the living body, storing means for storing a signal detected by the light receiving means every light receiving means and according to the progress of time, arithmetic means for converting to a signal according to measurement point every measurement point using the signal stored in the storing means and an image display generator that acquires the output of the arithmetic means as a signal at an estimated measurement point and displays an image as an intensity signal on a two-dimensional display screen and characterized in that wavelengths in accordance with the optical property of a measurement region are selected according to difference in the tissue of a measurement region.

(14) The optical system for measuring metabolism in a body based upon the optical systems described in above (12) and (13) and characterized in that an object of measurement is classified into regions and light of wavelengths preset every region is selected.

(15) The optical system for measuring metabolism in a body based upon the optical systems described in above (12) and (13) and characterized in that premeasurement using plural measuring wavelengths is made, an error of a signal to be measured (example: oxygenated hemoglobin) is evaluated and measuring wavelengths are selected based upon the error.

(16) The optical system for measuring metabolism in a body based upon the optical systems described in above (12) and (13) and characterized in that the characteristic of the tissue in each measurement position is acquired by a magnetic resonance imaging method and wavelengths are selected according to the characteristic.

(17) The optical system for measuring metabolism in a body based upon a method for measuring metabolism in a body for making radiated wavelengths variable in the optical systems described in above (12) to (16) and characterized in that a method of selecting light radiating means for radiating a suitable wavelength out of plural light radiating means provided beforehand or a method of providing a light source that can continuously vary a wavelength and setting and radiating a suitable wavelength or both methods is/are enabled.

According to the invention, as wavelengths according to a measurement region can be selected in consideration of difference in an optical property depending upon difference in the tissue even if distance between irradiation and detection is fixed and in addition, as wavelengths can be selected using an error in measuring the variation of the concentration of hemoglobin to be measured as a criterion, the optical technique for measuring metabolism in a body in which an error in measurement can be further reduced can be realized.

What is claimed is:

1. A biological photometric device comprising:
    a plurality of light sources for irradiating a head surface of a test body, each of the light sources irradiating a light of a different wavelength;
    a plurality of light detectors for detecting the lights emitted from said light sources and returned from the head surface; and
    a control device for calculating a concentration of metabolites in the head and changes in the concentration, said control device having selecting means for selecting a set of lights of different wavelengths from said light sources for irradiating towards different regions of the head surface for each test body to minimize a respective measurement noise thereof,
    wherein said light sources and said light detectors are adapted to be disposed on the head surface.

2. A biological photometric device according to claim 1, wherein said control device selects said set of lights of different wavelengths in accordance with a result of a premeasurement made before measuring the concentration.

3. A biological photometric device according to claim 1, further comprising a display for displaying a measurement result.

4. A biological photometric device comprising:
    a plurality of light sources for irradiating a head surface of a test body, each of the light sources being varied to irradiate lights of different wavelengths;
    a plurality of light detectors for detecting the lights emitted from said light sources and returned from the head surface; and
    a control device for calculating a concentration of metabolites in the head and changes in the concentration, said control device having selecting means for selecting a set of lights of different wavelengths from said light sources for irradiating towards different regions of the head surface for each test body to minimize a respective measurement noise thereof,
    wherein said light sources and said light detectors are adapted to be disposed on the head surface.

5. A biological photometric device according to claim 4, wherein said control device selects said lights of different wavelengths in accordance with a result of a premeasurement made before measuring the concentration.

6. A biological photometric device according to claim 4, further comprising a display for displaying a measurement result.

7. A biological photometric device comprising:
    a plurality of light sources for irradiating a head surface of a test body, each of the light sources irradiating a light of a different wavelength or being varied to irradiate lights of different wavelengths;
    a plurality of light detectors for detecting the lights emitted from said light sources and returned from the head surface; and
    a control device for calculating a concentration of metabolites in the head and changes in the concentration, said control device having selecting means for selecting a set of lights of different wavelengths from said light sources for irradiating towards different regions of the head surface for each test body in accordance with a result of a premeasurement made before measuring the concentration or a wavelength selected via an interface to minimize a respective measurement noise thereof,
    wherein said light sources and said light detectors are adapted to be disposed on the head surface.

* * * * *